(12) United States Patent
Dobie et al.

(10) Patent No.: US 7,163,927 B2
(45) Date of Patent: Jan. 16, 2007

(54) ANTISENSE MODULATION OF KINESIN-LIKE 1 EXPRESSION

(75) Inventors: Kenneth W. Dobie, Del Mar, CA (US); Erich Koller, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 77 days.

(21) Appl. No.: 10/156,603

(22) Filed: May 23, 2002

(65) Prior Publication Data

US 2003/0220275 A1    Nov. 27, 2003

(51) Int. Cl.
*A61K 31/70*   (2006.01)
*C07H 21/04*   (2006.01)
*C07H 21/02*   (2006.01)
*C12N 5/00*    (2006.01)
*C12Q 1/68*    (2006.01)

(52) U.S. Cl. ............................. 514/44; 435/6; 435/375; 435/377; 536/23.1; 536/24.1

(58) Field of Classification Search ................. 435/375, 435/377; 514/44; 536/23.1, 24.1, 24.5
See application file for complete search history.

(56) References Cited

U.S. PATENT DOCUMENTS

| | | | |
|---|---|---|---|
| 5,801,154 A | 9/1998 | Baracchini et al. ........... | 514/44 |
| 6,472,521 B1* | 10/2002 | Uhlmann et al. | |
| 2004/0009156 A1* | 1/2004 | Reinhard et al. ........ | 424/93.21 |

OTHER PUBLICATIONS

Blangy et al., *Phosphorylation by p34cdc2 regulates spindle association of human Eg5, a kinesin-related motor essential for bipolar spindle formation in vivo*, Cell, 1995, 83:1159-1169.

Ferhat et al., *Expression of the mitotic motor protein Eg5 in postmitotic neurons: implications for neuronal development*, J. Neurosci., 1998, 18:7822-7835.

Hansen et al., *Activation of Hex and mEg5 by retroviral insertion may contribute to mouse B-cell leukemia*, Oncogene, 1999, 18:6531-6539.

Kaiser et al., *All-trans-retinoic acid-mediated growth inhibition involves inhibition of human kinesin-related protein HsEg5*, J. Biol. Chem., 1999, 274:18925-18931.

Kapoor et al., *Probing spindle assembly mechanisms with monastrol, a small molecule inhibitor of the mitotic kinesin, Eg5*, J. Cell Biol., 2000, 150:975-988.

Mayer et al., *Small molecule inhibitor of mitotic spindle bipolarity identified in a phenotype-based screen*, Science, 1999, 286:971-974.

Miki et al., *All kinesin superfamily protein, KIF, genes in mouse and human*, Proc. Natl. Acad. Sci. U. S. A., 2001, 98:7004-7011.

Whitehead et al., *Expanding the role of HsEg5 within the mitotic and post-mitotic phases of the cell cycle*, J. Cell Sci., 1998, 111:2551-2561.

Whitehead et al., *The spindle kinesin-like protein HsEg5 is an autoantigen in systemic lupus erythematosus*, Arthritis Rheum., 1996, 39:1635-1642.

Agrawal S., et al., "Antisense therapeutics: is it as simple as complementary base recognition?" *Molecular Med. Today*, 2000, 6, 72-81.

Branch, A.D., "A good antisense molecule is hard to find," *TIBS*, 1998, 23, 45-50.

Jen, K.-Y., et al., "Suppression of gene expression by targeted disruption of messenger RNA: available options and current strategies," *Stem Cells*, 2000, 18, 307-319.

* cited by examiner

*Primary Examiner*—Sean McGarry
(74) *Attorney, Agent, or Firm*—Knobbe, Martens, Olson and Bear, LLP

(57) ABSTRACT

Antisense compounds, compositions and methods are provided for modulating the expression of kinesin-like 1. The compositions comprise antisense compounds, particularly antisense oligonucleotides, targeted to nucleic acids encoding kinesin-like 1. Methods of using these compounds for modulation of kinesin-like 1 expression and for treatment of diseases associated with expression of kinesin-like 1 are provided.

19 Claims, No Drawings

ANTISENSE MODULATION OF KINESIN-LIKE 1 EXPRESSION

FIELD OF THE INVENTION

The present invention provides compositions and methods for modulating the expression of kinesin-like 1. In particular, this invention relates to compounds, particularly oligonucleotides, specifically hybridizable with nucleic acids encoding kinesin-like 1. Such compounds have been shown to modulate the expression of kinesin-like 1.

BACKGROUND OF THE INVENTION

The intracellular transport of proteins, lipids, and mRNA to specific locations within the cell, as well as the proper alignment and separation of chromosomes in dividing cells, is essential to the functioning of the cell. The superfamily of proteins called kinesins (KIF), along with the myosins and dyneins, function as molecular engines to bind and transport vesicles and organelles along microtubules with energy supplied by ATP. KIFs have been identified in many species ranging from yeast to humans. The amino acid sequences which comprise the motor domain are highly conserved among eukaryotic phyla, while the region outside of the motor domain serves to bind to the cargo and varies in amino acid sequence among KIFs. The movement of a kinesin along a microtubule can occur in either the plus or minus direction, but any given kinesin can only travel in one direction, an action that is mediated by the polarity of the motor and the microtubule. The KIFs have been grouped into three major types depending on the position of the motor domain: the amino-terminal domain, the middle motor domain, and the carboxyl-terminal domain, referred to respectively as N-kinesin, M-kinesin, and C-kinesins. These are further classified into 14 classes based on a phylogenetic analysis of the 45 known human and mouse kinesin genes (Miki et al., *Proc. Natl. Acad. Sci. U.S.A.*, 2001, 98, 7004–7011).

One such kinesin, kinesin-like 1, a member of the N-2 (also called bimC) family of kinesins and is involved in separating the chromosomes by directing their movement along microtubules in the bipolar spindle. During mitosis, the microtubule bipolar spindle functions to distribute the duplicated chromosomes equally to daughter cells. Kinesin-like 1 is first phosphorylated by the kinase p34$^{cdc2}$ and is essential for centrosome separation and assembly of bipolar spindles at prophase (Blangy et al., *Cell*, 1995, 83, 1159–1169). In rodent neurons, kinesin-like 1 is expressed well past their terminal mitotic division, and has been implicated in regulating microtubule behaviors within the developing axons and dendrites (Ferhat et al., *J. Neurosci.*, 1998, 18, 7822–7835). The gene encoding human kinesin-like 1 (also called KNSL1, Eg5, HsEg5, HKSP, KIF11, thyroid interacting protein 5, and TRIP5) was cloned in 1995 (Blangy et al., *Cell*, 1995, 83, 1159–1169).

Inhibition of kinesin-like 1 has been suggested as a target for arresting cellular proliferation in cancer because of the central role kinesin-like 1 holds in mitosis. Expression of kinesin-like 1 may also contribute to other disease states. A contribution of kinesin-like 1 to B-cell leukemia has been demonstrated in mice as a result of upregulated expression of kinesin-like 1 following a retroviral insertion mutation in the proximity of the kinesin-like 1 gene (Hansen and Justice, *Oncogene*, 1999, 18, 6531–6539). Autoantibodies to a set of proteins in the mitotic spindle assembly have been detected in human sera and these autoantibodies have been associated with autoimmune diseases including carpal tunnel syndrome, Raynaud's phenomenon, systemic sclerosis, Sjorgren's syndrome, rheumatoid arthritis, polymyositis, and polyarteritis. One of these autoantigens is kinesin-like 1 and has been identified in systemic lupus erythematosus (Whitehead et al., *Arthritis Rheum.*, 1996, 39, 1635–1642).

Currently, there are no known therapeutic agents which effectively inhibit the synthesis of kinesin-like 1 and to date, investigative strategies aimed at modulating kinesin-like 1 function have involved antibodies, small molecules and one antisense expression vector.

The use of antibodies to kinesin-like 1 has been reported several times in the art as a method to examine the participation of kinesin-like 1 during different stages of mitosis (Blangy et al., *Cell*, 1995, 83, 1159–1169.; Kapoor et al., *J. Cell Biol.*, 2000, 150, 975–988.; Whitehead and Rattner, *J. Cell Sci.*, 1998, 111, 2551–2561). For instance, in the presence of antibodies specific to kinesin-like 1, microtubule arrays responsible for pre- and post-mitotic centrosome movement never form, confirming the recurring role of kinesin-like 1 in establishing the microtubule arrays that form during cell division. This role may also encompass the ability of kinesin-like 1 to influence the distribution of other protein components associated with cell division (Whitehead and Rattner, *J. Cell Sci.*, 1998, 111, 2551–2561).

The small molecule monastrol has been used in vitro as a useful and specific tool to probe the involvement of kinesin-like 1 in the mitotic process (Kapoor et al., *J. Cell Biol.*, 2000, 150, 975–988). Like the anti-kinesin-like 1 antibodies, the small molecule monastrol produces a monoastral phenotype, as opposed to the bipolar spindle, and subsequently arrests mitosis. The formation of the monastral spindle is reversible when monastrol is washed away, and the mechanism of monastrol action is presumed to be inhibition of kinesin-like 1 (Mayer et al., *Science*, 1999, 286, 971–974).

Another small molecule, all-trans-retinoic acid (ATRA) is able to arrest growth in a number of different cell types such as melanoma, lymphoma, neuroblastoma, embryonic stem, and carcinoma cells by modulating gene expression. Kinesin-like 1 is one of these target genes and the expression of kinesin-like 1 in pancreatic carcinoma cell lines is inhibited by ATRA at the posttranscriptional level. These anti-proliferative effects arising from ATRA inhibition of kinesin-like 1 was further confirmed by the use of an antisense expression vector directed against kinesin-like 1 (Kaiser et al., *J. Biol. Chem.*, 1999, 274, 18925–18931).

Consequently, there remains a long felt need for additional agents capable of effectively inhibiting kinesin-like 1 function.

Antisense technology is emerging as an effective means for reducing the expression of specific gene products and may therefore prove to be uniquely useful in a number of therapeutic, diagnostic, and research applications for the modulation of kinesin-like 1 expression.

The present invention provides compositions and methods for modulating kinesin-like 1 expression.

SUMMARY OF THE INVENTION

The present invention is directed to compounds, particularly antisense oligonucleotides, which are targeted to a nucleic acid encoding kinesin-like 1, and which modulate the expression of kinesin-like 1. Pharmaceutical and other compositions comprising the compounds of the invention are also provided. Further provided are methods of modulating the expression of kinesin-like 1 in cells or tissues comprising contacting said cells or tissues with one or more of the antisense compounds or compositions of the invention. Further provided are methods of treating an animal, particularly a human, suspected of having or being prone to a disease or condition associated with expression of kinesin-like 1 by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding kinesin-like 1, ultimately modulating the amount of kinesin-like 1 produced. This is accomplished by providing antisense compounds which specifically hybridize with one or more nucleic acids encoding kinesin-like 1. As used herein, the terms "target nucleic acid" and "nucleic acid encoding kinesin-like 1" encompass DNA encoding kinesin-like 1, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translocation of the RNA to sites within the cell which are distant from the site of RNA synthesis, translation of protein from the RNA, splicing of the RNA to yield one or more mRNA species, and catalytic activity which may be engaged in or facilitated by the RNA. The overall effect of such interference with target nucleic acid function is modulation of the expression of kinesin-like 1. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding kinesin-like 1. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding kinesin-like 1, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. mRNA transcripts produced via the process of splicing of two (or more) mRNAs from different gene sources are known as "fusion transcripts". It has also been found that introns can be effective, and therefore preferred, target regions for antisense compounds targeted, for example, to DNA or pre-mRNA.

It is also known in the art that alternative RNA transcripts can be produced from the same genomic region of DNA.

These alternative transcripts are generally known as "variants". More specifically, "pre-mRNA variants" are transcripts produced from the same genomic DNA that differ from other transcripts produced from the same genomic DNA in either their start or stop position and contain both intronic and extronic regions.

Upon excision of one or more exon or intron regions or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable.

An antisense compound is specifically hybridizable when binding of the compound to the target DNA or RNA molecule interferes with the normal function of the target DNA or RNA to cause a loss of activity, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed. It is preferred that the antisense compounds of the present invention comprise at least 80% sequence complementarity with the target nucleic acid, more that they comprise 90% sequence complementarity and even more comprise 95% sequence complementarity with the target nucleic acid sequence to which they are targeted. Percent complementarity of an antisense compound with a target nucleic acid can be determined routinely using basic local alignment search tools (BLAST programs) (Altschul et al., *J. Mol. Biol.,* 1990, 215, 403–410; Zhang and Madden, *Genome Res.,* 1997, 7, 649–656).

Antisense and other compounds of the invention, which hybridize to the target and inhibit expression of the target, are identified through experimentation, and representative sequences of these compounds are hereinbelow identified as preferred embodiments of the invention. The sites to which these preferred antisense compounds are specifically hybridizable are hereinbelow referred to as "preferred target regions" and are therefore preferred sites for targeting. As used herein the term "preferred target region" is defined as at least an 8-nucleobase portion of a target region to which an active antisense compound is targeted. While not wishing to be bound by theory, it is presently believed that these target regions represent regions of the target nucleic acid which are accessible for hybridization.

While the specific sequences of particular preferred target regions are set forth below, one of skill in the art will recognize that these serve to illustrate and describe particular embodiments within the scope of the present invention. Additional preferred target regions may be identified by one having ordinary skill.

Target regions 8–80 nucleobases in length comprising a stretch of at least eight (8) consecutive nucleobases selected from within the illustrative preferred target regions are considered to be suitable preferred target regions as well.

Exemplary good preferred target regions include DNA or RNA sequences that comprise at least the 8 consecutive nucleobases from the 5'-terminus of one of the illustrative preferred target regions (the remaining nucleobases being a consecutive stretch of the same DNA or RNA beginning immediately upstream of the 5'-terminus of the target region and continuing until the DNA or RNA contains about 8 to about 80 nucleobases). Similarly good preferred target regions are represented by DNA or RNA sequences that comprise at least the 8 consecutive nucleobases from the 3'-terminus of one of the illustrative preferred target regions (the remaining nucleobases being a consecutive stretch of the same DNA or RNA beginning immediately downstream of the 3'-terminus of the target region and continuing until the DNA or RNA contains about 8 to about 80 nucleobases). One having skill in the art, once armed with the empirically-derived preferred target regions illustrated herein will be able, without undue experimentation, to identify further preferred target regions. In addition, one having ordinary skill in the art will also be able to identify additional compounds, including oligonucleotide probes and primers, that specifically hybridize to these preferred target regions using techniques available to the ordinary practitioner in the art.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17–24; Celis, et al., *FEBS Lett.*, 2000, 480, 2–16), SAGE (serial analysis of gene expression) (Madden, et al., *Drug Discov. Today*, 2000, 5, 415–425), READS (restriction enzyme amplification of digested cDNAs) (Prashar and Weissman, *Methods Enzymol.*, 1999, 303, 258–72), TOGA (total gene expression analysis) (Sutcliffe, et al., *Proc. Natl. Acad. Sci. U.S.A.*, 2000, 97, 1976–81), protein arrays and proteomics (Celis, et al., *FEBS Lett.*, 2000, 480, 2–16; Jungblut, et al., *Electrophoresis*, 1999, 20, 2100–10), expressed sequence tag (EST) sequencing (Celis, et al., *FEBS Lett.*, 2000, 480, 2–16; Larsson, et al., *J. Biotechnol.*, 2000, 80, 143–57), subtractive RNA fingerprinting (SuRF) (Fuchs, et al., *Anal. Biochem.*, 2000, 286, 91–98; Larson, et al., *Cytometry*, 2000, 41, 203–208), subtractive cloning, differential display (DD) (Jurecic and Belmont, *Curr. Opin. Microbiol.*, 2000, 3, 316–21), comparative genomic hybridization (Carulli, et al., *J. Cell Biochem. Suppl.*, 1998, 31, 286–96), FISH (fluorescent in situ hybridization) techniques (Going and Gusterson, *Eur. J. Cancer*, 1999, 35, 1895–904) and mass spectrometry methods (reviewed in To, *Comb. Chem. High Throughput Screen*, 2000, 3, 235–41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 80 nucleobases (i.e. from about 8 to about 80 linked nucleosides). Particularly preferred antisense compounds are antisense oligonucleotides from about 8 to about 50 nucleobases, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

Antisense compounds 8–80 nucleobases in length comprising a stretch of at least eight (8) consecutive nucleobases selected from within the illustrative antisense compounds are considered to be suitable antisense compounds as well.

Exemplary preferred antisense compounds include DNA or RNA sequences that comprise at least the 8 consecutive nucleobases from the 5'-terminus of one of the illustrative preferred antisense compounds (the remaining nucleobases being a consecutive stretch of the same DNA or RNA beginning immediately upstream of the 5'-terminus of the antisense compound which is specifically hybridizable to the target nucleic acid and continuing until the DNA or RNA contains about 8 to about 80 nucleobases). Similarly preferred antisense compounds are represented by DNA or RNA sequences that comprise at least the 8 consecutive nucleobases from the 3'-terminus of one of the illustrative preferred antisense compounds (the remaining nucleobases being a consecutive stretch of the same DNA or RNA beginning immediately downstream of the 3'-terminus of the antisense compound which is specifically hybridizable to the target nucleic acid and continuing until the DNA or RNA contains about 8 to about 80 nucleobases). One having skill in the art, once armed with the empirically-derived preferred antisense compounds illustrated herein will be able, without undue experimentation, to identify further preferred antisense compounds.

Antisense and other compounds of the invention, which hybridize to the target and inhibit expression of the target, are identified through experimentation, and representative sequences of these compounds are herein identified as preferred embodiments of the invention. While specific sequences of the antisense compounds are set forth herein, one of skill in the art will recognize that these serve to illustrate and describe particular embodiments within the scope of the present invention. Additional preferred antisense compounds may be identified by one having ordinary skill.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric structure can be further joined to form a circular structure, however, open linear structures are generally preferred. In addition, linear structures may also have internal nucleobase complementarity and may therefore fold in a manner as to produce a double stranded structure. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science,* 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[$(CH_2)_n$O]$_m CH_3$, O$(CH_2)_n$O$CH_3$, O$(CH_2)_n$$NH_2$, O$(CH_2)_n$$CH_3$, O$(CH_2)_n$ON$H_2$, and O$(CH_2)_n$ON[$(CH_2)_n$ $CH_3$]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486–504) i.e., an alkoxyalkoxy group. A further preferred modification includes 2'-dimethylaminooxyethoxy, i.e., a O$(CH_2)_2$ON($CH_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$, also described in examples hereinbelow.

Other preferred modifications include 2'-methoxy (2'-O—CH$_3$), 2'-aminopropoxy (2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—CH$_2$—)$_n$ group bridging the 2' oxygen atom and the 4' carbon atom wherein n is 1 or 2. LNAs and preparation thereof are described in WO 98/39352 and WO 99/14226.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.,* 1994, 4, 1053–1060), a thioether, e.g., hexyl-S-tritylthiol (Manoharan et al., *Ann. N.Y. Acad. Sci.,* 1992, 660, 306–309; Manoharan et al., *Bioorg. Med. Chem. Let.,* 1993, 3, 2765–2770), a thiocholesterol (Oberhauser et al., *Nucl. Acids Res.,* 1992, 20, 533–538), an aliphatic chain, e.g., dodecandiol or undecyl residues (Saison-Behmoaras et al., *EMBO J.,* 1991, 10, 1111–1118; Kabanov et al., *FEBS Lett.,* 1990, 259, 327–330; Svinarchuk et al., *Biochimie,* 1993, 75, 49–54), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylaminocarbonyl-oxycholesterol moiety (Crooke et al., *J. Pharmacol. Exp. Ther.*, 1996, 277, 923–937). Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. The cleavage of RNA:RNA hybrids can, in like fashion, be accomplished through the actions of endoribonucleases, such as interferon-induced RNAseL which cleaves both cellular and viral RNA. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of kinesin-like 1 is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding kinesin-like 1, enabling sandwich and other assays to easily be constructed to exploit this fact. Hybridization of the antisense oligonucleotides of the invention with a nucleic acid encoding kinesin-like 1 can be detected by means known in the art. Such means may include conjugation of an enzyme to the oligonucleotide, radiolabelling of the oligonucleotide or any other suitable detection means. Kits using such detection means for detecting the level of kinesin-like 1 in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. application Ser. No. 08/886,829 (filed Jul. 1, 1997), U.S. application Ser. No. 09/108,673 (filed Jul. 1, 1998), U.S. application Ser. No. 09/256,515 (filed Feb. 23, 1999), U.S. application Ser. No. 09/082,624 (filed May 21, 1998) and U.S. application Ser. No. 09/315,298 (filed May 20, 1999), each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: non-ionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P.Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al). U.S. Pat. No. 5,540,935 (Miyazaki et al.) and U.S. Pat. No. 5,556,948

(Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems*, 1991, p.92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990, 7, 1–33; El Hariri et al., J. Pharm. Pharmacol., 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm. Exp. Ther.*, 1992, 263, 25; Yamashita et al., *J. Pharm. Sci.*, 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., *J. Control Rel.*, 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites are prepared as described in U.S. Pat. No. 5,506,351, herein incorporated by reference. For oligonucleotides synthesized using 2'-alkoxy amidites, optimized synthesis cycles were developed that incorporate multiple steps coupling longer wait times relative to standard synthesis cycles.

The following abbreviations are used in the text: thin layer chromatography (TLC), melting point (MP), high pressure liquid chromatography (HPLC), Nuclear Magnetic Resonance (NMR), argon (Ar), methanol (MeOH), dichloromethane ($CH_2Cl_2$), triethylamine (TEA), dimethyl formamide (DMF), ethyl acetate (EtOAc), dimethyl sulfoxide (DMSO), tetrahydrofuran (THF).

Oligonucleotides containing 5-methyl-2'-deoxycytidine (5-Me-dC) nucleotides were synthesized according to published methods (Sanghvi, et. al., *Nucleic Acids Research*, 1993, 21, 3197–3203) using commercially available phosphoramidites (Glen Research, Sterling Va. or ChemGenes, Needham Mass.) or prepared as follows:

Preparation of 5'-O-Dimethoxytrityl-thymidine intermediate for 5-methyl dC amidite To a 50 L glass reactor equipped with air stirrer and Ar gas line was added thymidine (1.00 kg, 4.13 mol) in anhydrous pyridine (6 L) at ambient temperature. Dimethoxytrityl (DMT) chloride (1.47 kg, 4.34 mol, 1.05 eq) was added as a solid in four portions over 1 h. After 30 min, TLC indicated approx. 95% product, 2% thymidine, 5% DMT reagent and by-products and 2% 3',5'-bis DMT product ($R_f$ in EtOAc 0.45, 0.05, 0.98, 0.95 respectively). Saturated sodium bicarbonate (4 L) and $CH_2Cl_2$ were added with stirring (pH of the aqueous layer 7.5). An additional 18 L of water was added, the mixture was stirred, the phases were separated, and the organic layer was transferred to a second 50 L vessel. The aqueous layer was extracted with additional $CH_2Cl_2$ (2×2 L). The combined organic layer was washed with water (10 L) and then concentrated in a rotary evaporator to approx. 3.6 kg total weight. This was redissolved in $CH_2Cl_2$ (3.5 L), added to the reactor followed by water (6 L) and hexanes (13 L). The mixture was vigorously stirred and seeded to give a fine white suspended solid starting at the interface. After stirring for 1 h, the suspension was removed by suction through a ½" diameter teflon tube into a 20 L suction flask, poured onto a 25 cm Coors Buchner funnel, washed with water (2×3 L) and a mixture of hexanes-$CH_2Cl_2$ (4:1, 2×3 L) and allowed to air dry overnight in pans (1" deep). This was further dried in a vacuum oven (75° C., 0.1 mm Hg, 48 h) to a constant weight of 2072 g (93%) of a white solid, (mp 122–124° C.). TLC indicated a trace contamination of the bis DMT product. NMR spectroscopy also indicated that 1–2 mole percent pyridine and about 5 mole percent of hexanes was still present.

Preparation of 5'-O-Dimethoxytrityl-2'-deoxy-5-methylcytidine intermediate for 5-methyl-dC amidite To a 50 L Schott glass-lined steel reactor equipped with an electric stirrer, reagent addition pump (connected to an addition funnel, heating/cooling system, internal thermometer and an Ar gas line was added 5'-O-dimethoxytrityl-thymidine (3.00 kg, 5.51 mol), anhydrous acetonitrile (25 L) and TEA (12.3 L, 88.4 mol, 16 eq). The mixture was chilled with stirring to −10° C. internal temperature (external −20° C.). Trimethylsilylchloride (2.1 L, 16.5 mol, 3.0 eq) was added over 30 minutes while maintaining the internal temperature below −5° C., followed by a wash of anhydrous acetonitrile (1 L). Note: the reaction is mildly exothermic and copious hydrochloric acid fumes form over the course of the addition. The reaction was allowed to warm to 0° C. and the reaction progress was confirmed by TLC (EtOAc-hexanes 4:1; $R_f$ 0.43 to 0.84 of starting material and silyl product, respectively). Upon completion, triazole (3.05 kg, 44 mol, 8.0 eq) was added the reaction was cooled to −20° C. internal temperature (external −30° C.). Phosphorous oxychloride (1035 mL, 11.1 mol, 2.01 eq) was added over 60 min so as to maintain the temperature between −20° C. and −10° C. during the strongly exothermic process, followed by a wash of anhydrous acetonitrile (1 L). The reaction was warmed to 0° C. and stirred for 1 h. TLC indicated a complete conversion to the triazole product ($R_f$ 0.83 to 0.34 with the product spot glowing in long wavelength UV light). The reaction mixture was a peach-colored thick suspension, which turned darker red upon warming without apparent decomposition. The reaction was cooled to −15° C. internal temperature and water (5 L) was slowly added at a rate to maintain the temperature below +10° C. in order to quench the reaction and to form a homogenous solution. (Caution: this reaction is initially very strongly exothermic). Approximately one-half of the reaction volume (22 L) was transferred by air pump to another vessel, diluted with EtOAc (12 L) and extracted with water (2×8 L). The combined water layers were back-extracted with EtOAc (6 L). The water layer was discarded and the organic layers were concentrated in a 20 L rotary evaporator to an oily foam. The foam was coevaporated with anhydrous acetonitrile (4 L) to remove EtOAc. (note: dioxane may be used instead of anhydrous acetonitrile if dried to a hard foam). The second half of the reaction was treated in the same way. Each residue was dissolved in dioxane (3 L) and concentrated ammonium hydroxide (750 mL) was added. A homogenous solution formed in a few minutes and the reaction was allowed to stand overnight (although the reaction is complete within 1 h).

TLC indicated a complete reaction (product $R_f$ 0.35 in EtOAc-MeOH 4:1). The reaction solution was concentrated on a rotary evaporator to a dense foam. Each foam was slowly redissolved in warm EtOAc (4 L; 50° C.), combined in a 50 L glass reactor vessel, and extracted with water (2×4L) to remove the triazole by-product. The water was back-extracted with EtOAc (2 L). The organic layers were combined and concentrated to about 8 kg total weight, cooled to 0° C. and seeded with crystalline product. After 24 hours, the first crop was collected on a 25 cm Coors Buchner funnel and washed repeatedly with EtOAc (3×3L) until a white powder was left and then washed with ethyl ether (2×3L). The solid was put in pans (1" deep) and allowed to air dry overnight. The filtrate was concentrated to an oil, then redissolved in EtOAc (2 L), cooled and seeded as before. The second crop was collected and washed as before (with proportional solvents) and the filtrate was first extracted with water (2×1L) and then concentrated to an oil. The residue was dissolved in EtOAc (1 L) and yielded a third crop which was treated as above except that more washing was required to remove a yellow oily layer.

After air-drying, the three crops were dried in a vacuum oven (50° C., 0.1 mm Hg, 24 h) to a constant weight (1750, 600 and 200 g, respectively) and combined to afford 2550 g (85%) of a white crystalline product (MP 215–217° C.) when TLC and NMR spectroscopy indicated purity. The mother liquor still contained mostly product (as determined by TLC) and a small amount of triazole (as determined by NMR spectroscopy), bis DMT product and unidentified minor impurities. If desired, the mother liquor can be purified by silica gel chromatography using a gradient of MeOH (0–25%) in EtOAc to further increase the yield.

Preparation of 5'-O-Dimethoxytrityl-2'-deoxy-N-4-benzoyl-5-methylcytidine penultimate intermediate for 5-methyl dC amidite Crystalline 5'-O-dimethoxytrityl-5-methyl-2'-deoxycytidine (2000 g, 3.68 mol) was dissolved in anhydrous DMF (6.0 kg) at ambient temperature in a 50 L glass reactor vessel equipped with an air stirrer and argon line. Benzoic anhydride (Chem Impex not Aldrich, 874 g, 3.86 mol, 1.05 eq) was added and the reaction was stirred at ambient temperature for 8 h. TLC ($CH_2Cl_2$-EtOAc; $CH_2Cl_2$-EtOAc 4:1; $R_f$ 0.25) indicated approx. 92% complete reaction. An additional amount of benzoic anhydride (44 g, 0.19 mol) was added. After a total of 18 h, TLC indicated approx. 96% reaction completion. The solution was diluted with EtOAc (20 L), TEA (1020 mL, 7.36 mol, ca 2.0 eq) was added with stirring, and the mixture was extracted with water (15 L, then 2×10 L). The aqueous layer was removed (no back-extraction was needed) and the organic layer was concentrated in 2×20 L rotary evaporator flasks until a foam began to form. The residues were coevaporated with acetonitrile (1.5 L each) and dried (0.1 mm Hg, 25° C., 24 h) to 2520 g of a dense foam. High pressure liquid chromatography (HPLC) revealed a contamination of 6.3% of N4, 3'-O-dibenzoyl product, but very little other impurities.

THe product was purified by Biotage column chromatography (5 kg Biotage) prepared with 65:35:1 hexanes-EtOAc-TEA (4L). The crude product (800 g), dissolved in $CH_2Cl_2$ (2 L), was applied to the column. The column was washed with the 65:35:1 solvent mixture (20 kg), then 20:80:1 solvent mixture (10 kg), then 99:1 EtOAc:TEA (17 kg). The fractions containing the product were collected, and any fractions containing the product and impurities were retained to be resubjected to column chromatography. The column was re-equilibrated with the original 65:35:1 solvent mixture (17 kg). A second batch of crude product (840 g) was applied to the column as before. The column was washed with the following solvent gradients: 65:35:1 (9 kg), 55:45:1 (20 kg), 20:80:1 (10 kg), and 99:1 EtOAc:TEA (15 kg). The column was reequilibrated as above, and a third batch of the crude product (850 g) plus impure fractions recycled from the two previous columns (28 g) was purified following the procedure for the second batch. The fractions containing pure product combined and concentrated on a 20L rotary evaporator, co-evaporated with acetontirile (3 L) and dried (0.1 mm Hg, 48 h, 25° C.) to a constant weight of 2023 g (85%) of white foam and 20 g of slightly contaminated product from the third run. HPLC indicated a purity of 99.8% with the balance as the diBenzoyl product.

[5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-methyl dC amidite)

5'-α-(4,4'-Dimethoxytriphenylmethyl)-2'-deoxy-$N^4$-benzoyl-5-methylcytidine (998 g, 1.5 mol) was dissolved in anhydrous DMF (2 L). The solution was co-evaporated with toluene (300 ml) at 50° C. under reduced pressure, then cooled to room temperature and 2-cyanoethyl tetraisopropylphosphorodiamidite (680 g, 2.26 mol) and tetrazole (52.5 g, 0.75 mol) were added. The mixture was shaken until all tetrazole was dissolved, N-methylimidazole (15 ml) was added and the mixture was left at room temperature for 5 hours. TEA (300 ml) was added, the mixture was diluted with DMF (2.5 L) and water (600 ml), and extracted with hexane (3×3 L). The mixture was diluted with water (1.2 L) and extracted with a mixture of toluene (7.5 L) and hexane (6 L). The two layers were separated, the upper layer was washed with DMF-water (7:3 v/v, 3×2 L) and water (3×2 L), and the phases were separated. The organic layer was dried ($Na_2SO_4$), filtered and rotary evaporated. The residue was co-evaporated with acetonitrile (2×2 L) under reduced pressure and dried to a constant weight (25° C., 0.1 mm Hg, 40 h) to afford 1250 g an off-white foam solid (96%).

2'-Fluoro amidites

2'-Fluorodeoxyadenosine amidites

2'-fluoro oligonucleotides were synthesized as described previously [Kawasaki, et. al., *J. Med. Chem.*, 1993, 36, 831–841] and U.S. Pat. No. 5,670,633, herein incorporated by reference. The preparation of 2'-fluoropyrimidines containing a 5-methyl substitution are described in U.S. Pat. No. 5,861,493. Briefly, the protected nucleoside N6-benzoyl-2'-deoxy-2'-fluoroadenosine was synthesized utilizing commercially available 9-beta-D-arabinofuranosyladenine as starting material and whereby the 2'-alpha-fluoro atom is introduced by a $S_N2$-displacement of a 2'-beta-triflate group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate isobutyrylarabinofuranosylguanosine. Alternatively, isobutyrylarabinofuranosylguanosine was prepared as described by Ross et al., (Nucleosides & Nucleosides, 16, 1645, 1997). Deprotection of the TPDS group was followed by protection of the hydroxyl group with THP to give isobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) modified amidites

2'-O-Methoxyethyl-substituted nucleoside amidites (otherwise known as MOE amidites) are prepared as follows, or alternatively, as per the methods of Martin, P., (Helvetica Chimica Acta, 1995, 78, 486–504).

Preparation of
2'-O-(2-methoxyethyl)-5-methyluridine intermediate 2,2'-Anhydro-5-methyl-uridine (2000 g, 8.32 mol), tris(2-methoxyethyl)borate (2504 g, 10.60 mol), sodium bicarbonate (60 g, 0.70 mol) and anhydrous 2-methoxyethanol (5 L) were combined in a 12 L three necked flask and heated to 130° C. (internal temp) at atmospheric pressure, under an argon atmosphere with stirring for 21 h. TLC indicated a complete reaction. The solvent was removed under reduced pressure until a sticky gum formed (50–85° C. bath temp and 100–11 mm Hg) and the residue was redissolved in water (3 L) and heated to boiling for 30 min in order the hydrolyze the borate esters. The water was removed under reduced pressure until a foam began to form and then the process was repeated. HPLC indicated about 77% product, 15% dimer (5' of product attached to 2' of starting material) and unknown derivatives, and the balance was a single unresolved early eluting peak.

The gum was redissolved in brine (3 L), and the flask was rinsed with additional brine (3 L). The combined aqueous solutions were extracted with chloroform (20 L) in a heavier-than continuous extractor for 70 h. The chloroform layer was concentrated by rotary evaporation in a 20 L flask to a sticky foam (2400 g). This was coevaporated with MeOH (400 mL) and EtOAc (8 L) at 75° C. and 0.65 atm until the foam dissolved at which point the vacuum was lowered to about 0.5 atm. After 2.5 L of distillate was collected a precipitate began to form and the flask was removed from the rotary evaporator and stirred until the suspension reached ambient temperature. EtOAc (2 L) was added and the slurry was filtered on a 25 cm table top Buchner funnel and the product was washed with EtOAc (3×2 L). The bright white solid was air dried in pans for 24 h then further dried in a vacuum oven (50° C., 0.1 mm Hg, 24 h) to afford 1649 g of a white crystalline solid (mp 115.5–116.5° C.).

The brine layer in the 20 L continuous extractor was further extracted for 72 h with recycled chloroform. The chloroform was concentrated to 120 g of oil and this was combined with the mother liquor from the above filtration (225 g), dissolved in brine (250 mL) and extracted once with chloroform (250 mL). The brine solution was continuously extracted and the product was crystallized as described above to afford an additional 178 g of crystalline product containing about 2% of thymine. The combined yield was 1827 g (69.4%). HPLC indicated about 99.5% purity with the balance being the dimer.

Preparation of 5'-O-DMT-2'-O-(2-methoxyethyl)-5-methyluridine penultimate intermediate In a 50 L glass-lined steel reactor, 2'-O-(2-methoxyethyl)-5-methyl-uridine (MOE-T, 1500 g, 4.738 mol), lutidine (1015 g, 9.476 mol) were dissolved in anhydrous acetonitrile (15 L). The solution was stirred rapidly and chilled to −10° C. (internal temperature). Dimethoxytriphenylmethyl chloride (1765.7 g, 5.21 mol) was added as a solid in one portion. The reaction was allowed to warm to −2° C. over 1 h. (Note: The reaction was monitored closely by TLC (EtOAc) to determine when to stop the reaction so as to not generate the undesired bis-DMT substituted side product). The reaction was allowed to warm from −2 to 3° C. over 25 min. then quenched by adding MeOH (300 mL) followed after 10 min by toluene (16 L) and water (16 L). The solution was transferred to a clear 50 L vessel with a bottom outlet, vigorously stirred for 1 minute, and the layers separated. The aqueous layer was removed and the organic layer was washed successively with 10% aqueous citric acid (8 L) and water (12 L). The product was then extracted into the aqueous phase by washing the toluene solution with aqueous sodium hydroxide (0.5N, 16 L and 8 L). The combined aqueous layer was overlayed with toluene (12 L) and solid citric acid (8 moles, 1270 g) was added with vigorous stirring to lower the pH of the aqueous layer to 5.5 and extract the product into the toluene. The organic layer was washed with water (10 L) and TLC of the organic layer indicated a trace of DMT-O-Me, bis DMT and dimer DMT.

The toluene solution was applied to a silica gel column (6 L sintered glass funnel containing approx. 2 kg of silica gel slurried with toluene (2 L) and TEA (25 mL)) and the fractions were eluted with toluene (12 L) and EtOAc (3×4 L) using vacuum applied to a filter flask placed below the column. The first EtOAc fraction containing both the desired product and impurities were resubjected to column chromatography as above. The clean fractions were combined, rotary evaporated to a foam, coevaporated with acetonitrile (6 L) and dried in a vacuum oven (0.1 mm Hg, 40 h, 40° C.) to afford 2850 g of a white crisp foam. NMR spectroscopy indicated a 0.25 mole % remainder of acetonitrile (calculates to be approx. 47 g) to give a true dry weight of 2803 g (96%). HPLC indicated that the product was 99.41% pure, with the remainder being 0.06 DMT-O—Me, 0.10 unknown, 0.44 bis DMT, and no detectable dimer DMT or 3'-O-DMT.

Preparation of [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite)

5'-O— (4,4'-Dimethoxytriphenylmethyl)-2-O-(2-methoxyethyl)-5-methyluridine (1237 g, 2.0 mol) was dissolved in anhydrous DMF (2.5 L). The solution was co-evaporated with toluene (200 ml) at 50° C. under reduced pressure, then cooled to room temperature and 2-cyanoethyl tetraisopropylphosphorodiamidite (900 g, 3.0 mol) and tetrazole (70 g, 1.0 mol) were added. The mixture was shaken until all tetrazole was dissolved, N-methylimidazole (20 ml) was added and the solution was left at room temperature for 5 hours. TEA (300 ml) was added, the mixture was diluted with DMF (3.5 L) and water (600 ml) and extracted with hexane (3×3L). The mixture was diluted with water (1.6 L) and extracted with the mixture of toluene (12 L) and hexanes (9 L). The upper layer was washed with DMF-water (7:3 v/v, 3×3 L) and water (3×3 L). The organic layer was dried ($Na_2SO_4$), filtered and evaporated. The residue was co-evaporated with acetonitrile (2×2 L) under reduced pressure and dried in a vacuum oven (25° C., 0.1 mm Hg, 40 h) to afford 1526 g of an off-white foamy solid (95%).

Preparation of 5'-O-Dimethoxytrityl-2'-O-(2-methoxyethyl)-5-methylcytidine intermediate To a 50 L Schott glass-lined steel reactor equipped with an electric stirrer, reagent addition pump (connected to an addition funnel), heating/cooling system, internal thermometer and argon gas line was added 5'-O-dimethoxytrityl-2'-O-(2-methoxyethyl)-5-methyl-uridine (2.616 kg, 4.23 mol, purified by base extraction only and no scrub column), anhydrous acetonitrile (20 L), and TEA (9.5 L, 67.7 mol, 16 eq). The mixture was chilled with stirring to −10° C. internal temperature (external −20° C.). Trimethylsilylchloride (1.60 L, 12.7 mol, 3.0 eq) was added over 30 min. while maintaining the internal temperature below −5° C., followed by a wash of anhydrous acetonitrile (1 L). (Note: the reaction is mildly exothermic and copious hydrochloric acid fumes form over the course of the addition). The reaction was allowed to warm to 0° C. and the reaction progress was confirmed by TLC (EtOAc, $R_f$ 0.68 and 0.87 for starting material and silyl product, respectively). Upon completion, triazole (2.34 kg, 33.8 mol, 8.0 eq) was added the reaction was cooled to −20° C. internal temperature (external −30° C.). Phosphorous oxychloride (793 mL, 8.51 mol, 2.01 eq) was added slowly over 60 min so as to maintain the temperature between −20° C. and −10° C. (note: strongly exothermic), followed by a wash of anhydrous acetonitrile (1 L). The reaction was warmed to 0° C. and stirred for 1 h, at which point it was an off-white thick suspension. TLC indicated a complete conversion to the triazole product (EtOAc, $R_f$ 0.87 to 0.75 with the product spot glowing in long wavelength UV light). The reaction was cooled to −15° C. and water (5 L) was slowly added at a rate to maintain the temperature below +10° C. in order to quench the reaction and to form a homogenous solution. (Caution: this reaction is initially very strongly exothermic). Approximately one-half of the reaction volume (22 L) was transferred by air pump to another vessel, diluted with EtOAc (12 L) and extracted with water (2×8 L). The second half of the reaction was treated in the same way. The combined aqueous layers were back-extracted with EtOAc (8 L) The organic layers were combined and concentrated in a 20 L rotary evaporator to an oily foam. The foam was coevaporated with anhydrous acetonitrile (4 L) to remove EtOAc. (note: dioxane may be used instead of anhydrous acetonitrile if dried to a hard foam). The residue was dissolved in dioxane (2 L) and concentrated ammonium hydroxide (750 mL) was added. A homogenous solution formed in a few minutes and the reaction was allowed to stand overnight TLC indicated a complete reaction ($CH_2Cl_2$-acetone-MeOH, 20:5:3, $R_f$ 0.51). The reaction solution was concentrated on a rotary evaporator to a dense foam and slowly redissolved in warm $CH_2Cl_2$ (4 L, 40° C.) and transferred to a 20 L glass extraction vessel equipped with a air-powered stirrer. The organic layer was extracted with water (2×6 L) to remove the triazole by-product. (Note: In the first extraction an emulsion formed which took about 2 h to resolve). The water layer was back-extracted with $CH_2Cl_2$ (2×2 L), which in turn was washed with water (3 L). The combined organic layer was concentrated in 2×20 L flasks to a gum and then recrystallized from EtOAc seeded with crystalline product. After sitting overnight, the first crop was collected on a 25 cm Coors Buchner funnel and washed repeatedly with EtOAc until a white free-flowing powder was left (about 3×3 L). The filtrate was concentrated to an oil recrystallized from EtOAc, and collected as above. The solid was air-dried in pans for 48 h, then further dried in a vacuum oven (50° C., 0.1 mm Hg, 17 h) to afford 2248 g of a bright white, dense solid (86%). An HPLC analysis indicated both crops to be 99.4% pure and NMR spectroscopy indicated only a faint trace of EtOAc remained.

Preparation of 5'-O-dimethoxytrityl-2'-O-(2-methoxyethyl)-N4-benzoyl-5-methyl-cytidine penultimate intermediate:

Crystalline 5'-O-dimethoxytrityl-2'-O-(2-methoxyethyl)-5-methyl-cytidine (1000 g, 1.62 mol) was suspended in anhydrous DMF (3 kg) at ambient temperature and stirred under an Ar atmosphere. Benzoic anhydride (439.3 g, 1.94 mol) was added in one portion. The solution clarified after 5 hours and was stirred for 16 h. HPLC indicated 0.45% starting material remained (as well as 0.32% N4, 3'-O-bis Benzoyl). An additional amount of benzoic anhydride (6.0 g, 0.0265 mol) was added and after 17 h, HPLC indicated no starting material was present. TEA (450 mL, 3.24 mol) and toluene (6 L) were added with stirring for 1 minute. The solution was washed with water (4×4 L), and brine (2×4 L). The organic layer was partially evaporated on a 20 L rotary evaporator to remove 4 L of toluene and traces of water. HPLC indicated that the bis benzoyl side product was present as a 6% impurity. The residue was diluted with toluene (7 L) and anhydrous DMSO (200 mL, 2.82 mol) and sodium hydride (60% in oil, 70 g, 1.75 mol) was added in one portion with stirring at ambient temperature over 1 h. The reaction was quenched by slowly adding then washing with aqueous citric acid (10%, 100 mL over 10 min, then 2×4 L), followed by aqueous sodium bicarbonate (2%, 2 L), water (2×4 L) and brine (4 L). The organic layer was concentrated on a 20 L rotary evaporator to about 2 L total volume. The residue was purified by silica gel column chromatography (6 L Buchner funnel containing 1.5 kg of silica gel wetted with a solution of EtOAc-hexanes-TEA (70:29:1)). The product was eluted with the same solvent (30 L) followed by straight EtOAc (6 L). The fractions containing the product were combined, concentrated on a rotary evaporator to a foam and then dried in a vacuum oven (50° C., 0.2 mm Hg, 8 h) to afford 1155 g of a crisp, white foam (98%). HPLC indicated a purity of >99.7%.

Preparation of [5'-O-(4,4'-Dimethoxytriphenylmethyl)-2'-O-(2-methoxyethyl)-$N^4$-benzoyl-5-methyl-cytidin-3'-O-yl]-2-cyanoethyl-N,N-diisopropylphosphoramidite (MOE 5-Me-C amidite)

5'-O— (4,4'-Dimethoxytriphenylmethyl)-2'-O-(2-methoxyethyl)-$N^4$-benzoyl-5-methylcytidine (1082 g, 1.5 mol) was dissolved in anhydrous DMF (2 L) and co-evaporated with toluene (300 ml) at 50° C. under reduced pressure. The mixture was cooled to room temperature and 2-cyanoethyl tetraisopropylphosphorodiamidite (680 g, 2.26 mol) and tetrazole (52.5 g, 0.75 mol) were added. The mixture was shaken until all tetrazole was dissolved, N-methylimidazole (30 ml) was added, and the mixture was left at room temperature for 5 hours. TEA (300 ml) was added, the mixture was diluted with DMF (1 L) and water (400 ml) and extracted with hexane (3×3 L). The mixture was diluted with water (1.2 L) and extracted with a mixture of toluene (9 L) and hexanes (6 L). The two layers were separated and the upper layer was washed with DMF-water (60:40 v/v, 3×3 L) and water (3×2 L). The organic layer was dried ($Na_2SO_4$), filtered and evaporated. The residue was co-evaporated with acetonitrile (2×2 L) under reduced pressure and dried in a vacuum oven (25° C., 0.1 mm Hg, 40 h) to afford 1336 g of an off-white foam (97%).

Preparation of [5'-O-(4,4'-Dimethoxytriphenylmethyl)-2'-O— (2-methoxyethyl)-$N^6$-benzoyladenosin-3'-O-yl]-2-cyanoethyl-N,N-diisopropylphosphoramidite (MOE A amdite)

5'-O-(4,4'-Dimethoxytriphenylmethyl)-2'-O-(2-methoxyethyl)-$N^6$-benzoyladenosine (purchased from Reliable Biopharmaceutical, St. Lois, Mo.), 1098 g, 1.5 mol) was dissolved in anhydrous DMF (3 L) and co-evaporated with toluene (300 ml) at 50° C. The mixture was cooled to room temperature and 2-cyanoethyl tetraisopropylphosphorodiamidite (680 g, 2.26 mol) and tetrazole (78.8 g, 1.24 mol) were added. The mixture was shaken until all tetrazole was dissolved, N-methylimidazole (30 ml) was added, and mixture was left at room temperature for 5 hours. TEA (300 ml) was added, the mixture was diluted with DMF (1 L) and water (400 ml) and extracted with hexanes (3×3 L). The mixture was diluted with water (1.4 L) and extracted with the mixture of toluene (9 L) and hexanes (6 L). The two layers were separated and the upper layer was washed with DMF-water (60:40, v/v, 3×3 L) and water (3×2 L). The organic layer was dried ($Na_2SO_4$), filtered and evaporated to a sticky foam. The residue was co-evaporated with acetonitrile (2.5 L) under reduced pressure and dried in a vacuum oven (25° C., 0.1 mm Hg, 40 h) to afford 1350 g of an off-white foam solid (96%).

Prepartion of [5'-O-(4,4'-Dimethoxytriphenylmethyl)-2'-O—(2-methoxyethyl)-N$^4$-isobutyrylguanosin-3'-O-yl]-2-cyanoethyl-N,N-diisopropylphosphoramidite (MOE G amidite)

5'-O-(4,4'-Dimethoxytriphenylmethyl)-2'-O-(2-methoxyethyl)-N$^4$-isobutyrlguanosine (purchased from Reliable Biopharmaceutical, St. Louis, Mo., 1426 g, 2.0 mol) was dissolved in anhydrous DMF (2 L). The solution was co-evaporated with toluene (200 ml) at 50° C., cooled to room temperature and 2-cyanoethyl tetraisopropylphosphorodiamidite (900 g, 3.0 mol) and tetrazole (68 g, 0.97 mol) were added. The mixture was shaken until all tetrazole was dissolved, N-methylimidazole (30 ml) was added, and the mixture was left at room temperature for 5 hours. TEA (300 ml) was added, the mixture was diluted with DMF (2 L) and water (600 ml) and extracted with hexanes (3×3 L). The mixture was diluted with water (2 L) and extracted with a mixture of toluene (10 L) and hexanes (5 L). The two layers were separated and the upper layer was washed with DMF-water (60:40, v/v, 3×3 L). EtOAc (4 L) was added and the solution was washed with water (3×4 L). The organic layer was dried (Na$_2$SO$_4$), filtered and evaporated to approx. 4 kg. Hexane (4 L) was added, the mixture was shaken for 10 min, and the supernatant liquid was decanted. The residue was co-evaporated with acetonitrile (2×2 L) under reduced pressure and dried in a vacuum oven (25° C., 0.1 mm Hg, 40 h) to afford 1660 g of an off-white foamy solid (91%).

2'-O-(Aminooxyethyl) nucleoside amidites and 2'-O-(dimethylaminooxyethyl) nucleoside amidites 2'-(Dimethylaminooxyethoxy) Nucleoside amidites 2'-(Dimethylaminooxyethoxy) nucleoside amidites (also known in the art as 2'-O-(dimethylaminooxyethyl) nucleoside amidites) are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O$^2$-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC (R$_f$ 0.22, EtOAc) indicated a complete reaction. The solution was concentrated under reduced pressure to a thick oil. This was partitioned between CH$_2$Cl$_2$ (1 L) and saturated sodium bicarbonate (2×1 L) and brine (1 L). The organic layer was dried over sodium sulfate, filtered, and concentrated under reduced pressure to a thick oil. The oil was dissolved in a 1:1 mixture of EtOAc and ethyl ether (600 mL) and cooling the solution to −10° C. afforded a white crystalline solid which was collected by filtration, washed with ethyl ether (3×200 mL) and dried (40° C., 1 mm Hg, 24 h) to afford 149 g of white solid (74.8%). TLC and NMR spectroscopy were consistent with pure product.

5'-O-tert-Butyldiphenylsilyl-2'-O-(2-hydroxyethyl)-5-methyluridine

In the fume hood, ethylene glycol (350 mL, excess) was added cautiously with manual stirring to a 2 L stainless steel pressure reactor containing borane in tetrahydrofuran (1.0 M, 2.0 eq, 622 mL). (Caution: evolves hydrogen gas). 5'-O-tert-Butyldiphenylsilyl-O$^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient temperature and opened. TLC (EtOAc, R$_f$ 0.67 for desired product and R$_f$ 0.82 for ara-T side product) indicated about 70% conversion to the product. The solution was concentrated under reduced pressure (10 to 1 mm Hg) in a warm water bath (40–100° C.) with the more extreme conditions used to remove the ethylene glycol. (Alternatively, once the THF has evaporated the solution can be diluted with water and the product extracted into EtOAc). The residue was purified by column chromatography (2 kg silica gel, EtOAc-hexanes gradient 1:1 to 4:1). The appropriate fractions were combined, evaporated and dried to afford 84 g of a white crisp foam (50%), contaminated starting material (17.4 g, 12% recovery) and pure reusable starting material (20 g, 13% recovery). TLC and NMR spectroscopy were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol) and dried over P$_2$O$_5$ under high vacuum for two days at 40° C. The reaction mixture was flushed with argon and dissolved in dry THF (369.8 mL, Aldrich, sure seal bottle). Diethyl-azodicarboxylate (6.98 mL, 44.36 mmol) was added dropwise to the reaction mixture with the rate of addition maintained such that the resulting deep red coloration is just discharged before adding the next drop. The reaction mixture was stirred for 4 hrs., after which time TLC (EtOAc:hexane, 60:40) indicated that the reaction was complete. The solvent was evaporated in vacuuo and the residue purified by flash column chromatography (eluted with 60:40 EtOAc:hexane), to yield 2'-O-([2-phthalimidoxy)ethyl]-5'-t-butyldiphenylsilyl-5-methyluridine as white foam (21.819 g, 86%) upon rotary evaporation.

5'-O-tert-butyldiphenylsilyl-2'-O-[(2-formadoximinooxy)ethyl]-5-methyluridine

2'-O-([2-phthalimidoxy)ethyl]-5'-t-butyldiphenylsilyl-5-methyluridine (3.1 g, 4.5 mmol) was dissolved in dry CH$_2$Cl$_2$ (4.5 mL) and methylhydrazine (300 mL, 4.64 mmol) was added dropwise at −10° C. to 0° C. After 1 h the mixture was filtered, the filtrate washed with ice cold CH$_2$Cl$_2$, and the combined organic phase was washed with water and brine and dried (anhydrous Na$_2$SO$_4$). The solution was filtered and evaporated to afford 2'-O-(aminooxyethyl) thymidine, which was then dissolved in MeOH (67.5 mL). Formaldehyde (20% aqueous solution, w/w, 1.1 eq.) was added and the resulting mixture was stirred for 1 h. The solvent was removed under vacuum and the residue was purified by column chromatography to yield 5'-O-tert-butyldiphenylsilyl-2'-O-[(2-formadoximinooxy) ethyl]-5-methyluridine as white foam (1.95 g, 78%) upon rotary evaporation.

5'-O-tert-Butyldiphenylsilyl-2'-O-[N,N dimethylaminooxyethyl]-5-methyluridine 5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL) and cooled to 10° C. under inert atmosphere. Sodium cyanoborohydride (0.39 g, 6.13 mmol) was added and the reaction mixture was stirred. After 10 minutes the reaction was warmed to room temperature and stirred for 2 h. while the progress of the reaction was monitored by TLC (5% MeOH in $CH_2Cl_2$). Aqueous $NaHCO_3$ solution (5%, 10 mL) was added and the product was extracted with EtOAc (2×20 mL). The organic phase was dried over anhydrous $Na_2SO_4$, filtered, and evaporated to dryness. This entire procedure was repeated with the resulting residue, with the exception that formaldehyde (20% w/w, 30 mL, 3.37 mol) was added upon dissolution of the residue in the PPTS/MeOH solution. After the extraction and evaporation, the residue was purified by flash column chromatography and (eluted with 5% MeOH in $CH_2Cl_2$) to afford 5'-O-tert-butyldiphenylsilyl-2'-O-[N,N-dimethylaminooxyethyl]-5-methyluridine as a white foam (14.6 g, 80%) upon rotary evaporation.

2'-O-(dimethylaminooxyethyl)-5-methyluridine

Triethylamine trihydrofluoride (3.91 mL, 24.0 mmol) was dissolved in dry THF and TEA (1.67 mL, 12 mmol, dry, stored over KOH) and added to 5'-O-tert-butyldiphenylsilyl-2'-O-[N,N-dimethylaminooxyethyl]-5-methyluridine (1.40 g, 2.4 mmol). The reaction was stirred at room temperature for 24 hrs and monitored by TLC (5% MeOH in $CH_2Cl_2$). The solvent was removed under vacuum and the residue purified by flash column chromatography (eluted with 10% MeOH in $CH_2Cl_2$) to afford 2'-O-(dimethylaminooxyethyl)-5-methyluridine (766 mg, 92.5%) upon rotary evaporation of the solvent.

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40° C., co-evaporated with anhydrous pyridine (20 mL), and dissolved in pyridine (11 mL) under argon atmosphere. 4-dimethylaminopyridine (26.5 mg, 2.60 mmol) and 4,4'-dimethoxytrityl chloride (880 mg, 2.60 mmol) were added to the pyridine solution and the reaction mixture was stirred at room temperature until all of the starting material had reacted. Pyridine was removed under vacuum and the residue was purified by column chromatography (eluted with 10% MeOH in $CH_2Cl_2$ containing a few drops of pyridine) to yield 5'-O-DMT-2'-O-(dimethylamino-oxyethyl)-5-methyluridine (1.13 g, 80%) upon rotary evaporation.

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL), N,N-diisopropylamine tetrazonide (0.29 g, 1.67 mmol) was added and the mixture was dried over $P_2O_5$ under high vacuum overnight at 40° C. This was dissolved in anhydrous acetonitrile (8.4 mL) and 2-cyanoethyl-N,N,N,N-tetraisopropylphosphoramidite (2.12 mL, 6.08 mmol) was added. The reaction mixture was stirred at ambient temperature for 4 h under inert atmosphere. The progress of the reaction was monitored by TLC (hexane:EtOAc 1:1). The solvent was evaporated, then the residue was dissolved in EtOAc (70 mL) and washed with 5% aqueous $NaHCO_3$ (40 mL). The EtOAc layer was dried over anhydrous $Na_2SO_4$, filtered, and concentrated. The residue obtained was purified by column chromatography (EtOAc as eluent) to afford 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%) upon rotary evaporation.

2'-(Aminooxyethoxy) Nucleoside amidites

2'-(Aminooxyethoxy) nucleoside amidites (also known in the art as 2'-O-(aminooxyethyl) nucleoside amidites) are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 Al 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine, which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may be phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) Nucleoside amidites

2'-dimethylaminoethoxyethoxy nucleoside amidites (also known in the art as 2'-O-dimethylaminoethoxyethyl, i.e., 2'-O—$CH_2$—O—$CH_2$—$N(CH_2)_2$, or 2'-DMAEOE nucleoside amidites) are prepared as follows. Other nucleoside amidites are prepared similarly.

2'-O-[2(2-N,N-dimethylaminoethoxy)ethyl]-5-methyl Uridine

2[2-(Dimethylamino)ethoxy]ethanol (Aldrich, 6.66 g, 50 mmol) was slowly added to a solution of borane in tetrahydrofuran (1 M, 10 mL, 10 mmol) with stirring in a 100 mL bomb. (Caution: Hydrogen gas evolves as the solid dissolves). $O^2$-,2'-anhydro-5-methyluridine (1.2 g, 5 mmol), and sodium bicarbonate (2.5 mg) were added and the bomb was sealed, placed in an oil bath and heated to 155° C. for 26 h. then cooled to room temperature. The crude solution was concentrated, the residue was diluted with water (200 mL) and extracted with hexanes (200 mL). The product was extracted from the aqueous layer with EtOAc (3×200 mL) and the combined organic layers were washed once with water, dried over anhydrous sodium sulfate, filtered and concentrated. The residue was purified by silica gel column chromatography (eluted with 5:100:2 MeOH/$CH_2Cl_2$/TEA) as the eluent. The appropriate fractions were combined and evaporated to afford the product as a white solid.

5'-O-dimethoxytrityl-2'-O-[2(2-N,N-dimethylaminoethoxy) ethyl)]-5-methyl uridine To 0.5 g (1.3 mmol) of 2'-O-[2(2-N,N-dimethylaminoethoxy)ethyl)]-5-methyl uridine in anhydrous pyridine (8 mL), was added TEA (0.36 mL) and dimethoxytrityl chloride (DMT-Cl, 0.87 g, 2 eq.) and the reaction was stirred for 1 h. The reaction mixture was poured into water (200 mL) and extracted with $CH_2Cl_2$ (2×200 mL). The combined $CH_2Cl_2$ layers were washed with saturated $NaHCO_3$ solution, followed by saturated NaCl solution, dried over anhydrous sodium sulfate, filtered and evaporated. The residue was purified by silica gel column chromatography (eluted with 5:100:1 MeOH/$CH_2Cl_2$/TEA) to afford the product.

5'-O-Dimethoxytrityl-2'-O-[2(2-N,N-dimethylaminoethoxy)ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) were added to a solution of 5'-O-dimethoxytrityl-2'-O-[2(2-N,N-dimethylaminoethoxy)ethyl)]-5-methyluridine (2.17 g, 3 mmol) dissolved in $CH_2Cl_2$ (20 mL) under an atmosphere of argon. The reaction mixture was stirred overnight and the solvent evaporated. The resulting residue was purified by silica gel column chromatography with EtOAc as the eluent to afford the title compound.

Example 2

Oligonucleotide Synthesis

Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12–16 hr), the oligonucleotides were recovered by precipitating with >3 volumes of ethanol from a 1 M $NH_4OAc$ solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3

Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4

PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphor-amidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12–16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-0-(methoxyethyl) amidites for the 2'-O-methyl amidites.

[2'-O— (2-methoxyethyl) Phosphodiester]-[2'-deoxy Phosphorothioate]-[2'-O— (2-Methoxyethyl) Phosphodiester] Chimeric Oligonucleotides

[2'-O-(2-methoxyethyl phosphodiester]-[2'-deoxy phosphorothioate]-[2'-O— (methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass solid support and deblocking in concentrated ammonium hydroxide at 55° C. for 12–16 hours, the oligonucleotides or oligonucleosides are recovered by precipitation out of 1 M $NH_4OAc$ with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32+/−48). For some studies oligonucleotides were purified by HPLC, as described by Chiang et al., *J. Biol. Chem.* 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

T47D Cells:

The T47D breast adenocarcinoma cells were obtained from the American Type Culture Collection (ATCC) (Manassas, Va.). Cells were cultured in Gibco DMEM High glucose media supplemented with 10% FBS.

For cell cycle assays, cells are plated in 24-well plates at 170,000 cells per well.

MCF7:

The human breast carcinoma cell line MCF-7 was obtained from the American Type Culture Collection (Manassas, Va.). MCF-7 cells were routinely cultured in DMEM low glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For cell cycle assays, cells are plated in 24-well plates at 140,000 cells per well.

HMEC:

The human mammary epithelial cell line HMEC was obtained from BioWhittacker (Clonetics). HMEC cells were routinely cultured in Mammary Epithelial Growth Medium, BioWhittacker (Clonetics). Cells were routinely passaged by trypsinization and dilution when they reached 70% confluence. Cells were seeded into 24-well plates (Nunc-Nuncolon cat. #143982) at a density of 60,000 cells/well for use in subsequent analyses.

For Northern blotting or other analyses, cells may be seeded onto 100 mm or other standard tissue culture plates and treated similarly, using appropriate volumes of medium and oligonucleotide.

Treatment with Antisense Compounds:

When cells reached 70% confluency, they were treated with oligonucleotide. For cells grown in 96-well plates, wells were washed once with 100 μL OPTI-MEM™-1 reduced-serum medium (Invitrogen Corporation, Carlsbad, Calif.) and then treated with 130 μL of OPTI-MEM™-1 containing 3.75 μg/mL LIPOFECTIN™ (Invitrogen Corporation, Carlsbad, Calif.) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments.

Example 10

Analysis of Oligonucleotide Inhibition of Kinesin-Like 1 Expression

Antisense modulation of kinesin-like 1 expression can be assayed in a variety of ways known in the art. For example, kinesin-like 1 mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of kinesin-like 1 can be quantitated in a variety of ways well known in the art, such as immunoprecipitation, Western blot analysis (immunoblotting), ELISA or fluorescence-activated cell sorting (FACS). Antibodies directed to kinesin-like 1 can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., (*Current Protocols in Molecular Biology*, Volume 2, pp. 11.12.1–11.12.9, John Wiley & Sons, Inc., 1997). Preparation of monoclonal antibodies is taught in, for example, Ausubel, F. M. et al., (*Current Protocols in Molecular Biology*, Volume 2, pp. 11.4.1–11.11.5, John Wiley & Sons, Inc., 1997).

Immunoprecipitation methods are standard in the art and can be found at, for example, Ausubel, F. M. et al., (*Current Protocols in Molecular Biology*, Volume 2, pp. 10.16.1–10.16.11, John Wiley & Sons, Inc., 1998). Western blot (immunoblot) analysis is standard in the art and can be found at, for example, Ausubel, F. M. et al., (*Current Protocols in Molecular Biology*, Volume 2, pp. 10.8.1–10.8.21, John Wiley & Sons, Inc., 1997). Enzyme-linked immunosorbent assays (ELISA) are standard in the art and can be found at, for example, Ausubel, F. M. et al., (*Current Protocols in Molecular Biology*, Volume 2, pp. 11.2.1–11.2.22, John Wiley & Sons, Inc., 1991).

Example 11

Poly(A)+ mRNA Isolation

Poly(A)+ mRNA was isolated according to Miura et al., (*Clin. Chem.*, 1996, 42, 1758–1764). Other methods for poly(A)+ mRNA isolation are taught in, for example, Ausubel, F. M. et al., (*Current Protocols in Molecular Biology*, Volume 1, pp. 4.5.1–4.5.3, John Wiley & Sons, Inc., 1993). Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 170 µL water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-Time Quantitative PCR Analysis of Kinesin-Like 1 mRNA Levels

Quantitation of kinesin-like 1 mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 µL PCR cocktail (2.5×PCR buffer (—MgC12), 6.6 mM MgC12, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution. The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreenTM (Molecular Probes, Inc. Eugene, Oreg.). GAPDH expression is quantified by real time RT-PCR, by being run simultaneously with the target, multiplexing, or separately. Total RNA is quantified using RiboGreenTM RNA quantification reagent from Molecular Probes. Methods of RNA quantification by RiboGreenTM are taught in Jones, L. J., et al, (*Analytical Biochemistry*, 1998, 265, 368–374).

In this assay, 170 µL of RiboGreenTM working reagent (RiboGreenTM reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 480 nm and emission at 520 nm.

Probes and primers to human kinesin-like 1 were designed to hybridize to a human kinesin-like 1 sequence, using published sequence information (GenBank accession number NM_004523.1, incorporated herein as SEQ ID NO:3). For human kinesin-like 1 the PCR primers were:

forward primer: GTGGTGAGATGCAGACCATTTAAT (SEQ ID NO: 4)

reverse primer: CTTTTCGTACAGGATCACATTCTAC-TATTG (SEQ ID NO: 5)

and the PCR probe was: FAM-TGGCAGAGCG-GAAAGCTAGCGC-TAMRA ( ) where FAM is the fluorescent dye and TAMRA is the quencher dye. For human GAPDH the PCR primers were:

forward primer: GAAGGTGAAGGTCGGAGTC(SEQ ID NO:7)

reverse primer: GAAGATGGTGATGGGATTTC (SEQ ID NO:8) and the PCR probe was: 5' JOE-CAAGCTTC-CCGTTCTCAGCC-TAMRA 3' (SEQ ID NO: 9) where JOE is the fluorescent reporter dye and TAMRA is the quencher dye.

Example 14

Northern Blot Analysis of Kinesin-Like 1 mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™–N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human kinesin-like 1, a human kinesin-like 1 specific probe was prepared by PCR using the forward primer GTGGTGAGATGCAGACCATTTAAT (SEQ ID NO: 4) and the reverse primer CTTTTCGTACAGGATCA-CATTCTACTATTG (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense inhibition of human kinesin-like 1 expression by chimeric phosphorothioate oligonucleotides having 2'-MOE wings and a deoxy gap In accordance with the present invention, a series of oligonucleotides were designed to target different regions of the human kinesin-like 1 RNA, using published sequences (GenBank accession number NM_004523.1, incorporated herein as SEQ ID NO: 3). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on human kinesin-like 1 mRNA levels by quantitative real-time PCR as described in other examples herein. Data are averages from two experiments in which T-24 cells were treated with the antisense oligonucleotides of the present invention. If present, "N.D." indicates "no data".

TABLE 1

Inhibition of human kinesin-like 1 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 183876 | Coding | 3 | 2284 | tgttgactatatccttagat | 44 | 10 |
| 183877 | Coding | 3 | 1838 | tctgctgctaatgattgttc | 79 | 11 |
| 183878 | Coding | 3 | 1771 | ctggaatagatgtgagagat | 78 | 12 |
| 183879 | Coding | 3 | 875 | aaagtcaacagggattgatt | 69 | 13 |
| 183880 | Coding | 3 | 2641 | gatcaagaaaaatgttatgc | 62 | 14 |
| 183881 | Coding | 3 | 1753 | atccaagtgctactgtagta | 86 | 15 |
| 183882 | Coding | 3 | 1027 | tttcctcaagattgagagat | 78 | 16 |
| 183883 | Coding | 3 | 2202 | caaagcacagaatctctctg | 68 | 17 |
| 183884 | Coding | 3 | 2172 | cattaacttgcaaagttcct | 58 | 18 |
| 183885 | Coding | 3 | 1545 | atccagtttggaatggagac | 43 | 19 |
| 183886 | Coding | 3 | 2881 | ttagcatcattaacagctca | 72 | 20 |
| 183887 | Coding | 3 | 1312 | taaacaactctgtaacccta | 41 | 21 |
| 183888 | Coding | 3 | 528 | agaaacatcagatgatggat | 82 | 22 |
| 183889 | Coding | 3 | 1898 | agtgaacttagaagatcagt | 66 | 23 |
| 183890 | Coding | 3 | 2849 | ttcagctgatcaaggagatg | 64 | 24 |
| 183891 | Coding | 3 | 840 | ccgagctctcttatcaacag | 81 | 25 |
| 183892 | Coding | 3 | 1581 | agcttctgcattgtgttggt | 76 | 26 |
| 183893 | 3'UTR | 3 | 3597 | attcaactgaatttacagta | 56 | 27 |
| 183894 | Coding | 3 | 3144 | cagaggtaatctgctctttg | 66 | 28 |
| 183895 | Coding | 3 | 1341 | acactggtcaagttcatttt | 74 | 29 |
| 183896 | Coding | 3 | 1456 | cagtactttccaaagctgat | 40 | 30 |
| 183897 | Coding | 3 | 2119 | cagttaggtttccacattgc | 77 | 31 |
| 183898 | 3'UTR | 3 | 3707 | ctactttatatgaaaactag | 30 | 32 |
| 183899 | Coding | 3 | 1053 | atgagcatattccaatgtac | 76 | 33 |

TABLE 1-continued

Inhibition of human kinesin-like 1 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 183900 | Coding | 3 | 536 | agtctctcagaaacatcaga | 67 | 34 |
| 183901 | Coding | 3 | 394 | taccagccaagggatcctct | 79 | 35 |
| 183902 | Coding | 3 | 489 | ttcattatagatctccaaca | 39 | 36 |
| 183903 | Coding | 3 | 1619 | ttaaacagactattcaggtt | 64 | 37 |
| 183904 | Coding | 3 | 2960 | tcttcagtatactgccccag | 72 | 38 |
| 183905 | Coding | 3 | 2301 | actgtgaaaagtcattttgt | 48 | 39 |
| 183906 | Coding | 3 | 1159 | caagatctcgttttaaacgt | 76 | 40 |
| 183907 | Coding | 3 | 308 | tggccatacgcaaagatagt | 34 | 41 |
| 183908 | Coding | 3 | 2260 | gctgtatattttcctggaca | 76 | 42 |
| 183909 | Coding | 3 | 1659 | ttgctttgagctgccatcct | 0 | 43 |
| 183910 | Coding | 3 | 2333 | gagaagccatcagaatcagc | 71 | 44 |
| 183911 | Coding | 3 | 1023 | ctcaagattgagagatgcag | 79 | 45 |
| 183912 | Coding | 3 | 2620 | gtttctcatgagctgcctta | 71 | 46 |

As shown in Table 1, SEQ ID NOs 11, 12, 13, 14, 15, 16, 17, 20, 22, 23, 24, 25, 26, 28, 29, 31, 33, 34, 35, 37, 38, 40, 42, 44, 45 and 46 demonstrated at least 61% inhibition of human kinesin-like 1 expression in this assay and are therefore preferred. The target sites to which these preferred sequences are complementary are herein referred to as "preferred target regions" and are therefore preferred sites for targeting by compounds of the present invention.

TABLE 2

Sequence and position of preferred target regions identified in kinesin-like 1.

| SITEID | TARGET SEQ ID NO | TARGET SITE | SEQUENCE | REV COMP OF SEQ ID | ACTIVE IN | SEQ ID NO |
|---|---|---|---|---|---|---|
| 99215 | 3 | 1838 | gaacaatcattagcagcaga | 11 | H. sapiens | 47 |
| 99216 | 3 | 1771 | atctctcacatctattccag | 12 | H. sapiens | 48 |
| 99217 | 3 | 875 | aatcaatccctgttgacttt | 13 | H. sapiens | 49 |
| 99218 | 3 | 2641 | gcataacattttctcttgatc | 14 | H. sapiens | 50 |
| 99219 | 3 | 1753 | tactacagtagcacttggat | 15 | H. sapiens | 51 |
| 99220 | 3 | 1027 | atctctcaatcttgaggaaa | 16 | H. sapiens | 52 |
| 99221 | 3 | 2202 | cagagagattctgtgctttg | 17 | H. sapiens | 53 |
| 99224 | 3 | 2881 | tgagctgttaatgatgctaa | 20 | H. sapiens | 54 |
| 99226 | 3 | 528 | atccatcatctgatgtttct | 22 | H. sapiens | 55 |
| 99227 | 3 | 1898 | actgatcttctaagttcact | 23 | H. sapiens | 56 |
| 99228 | 3 | 2849 | catctccttgatcagctgaa | 24 | H. sapiens | 57 |
| 99229 | 3 | 840 | ctgttgataagagagctcgg | 25 | H. sapiens | 58 |
| 99230 | 3 | 1581 | accaacacaatgcagaagct | 26 | H. sapiens | 59 |
| 99232 | 3 | 3144 | caaagagcagattacctctg | 28 | H. sapiens | 60 |

TABLE 2-continued

Sequence and position of preferred target regions identified in kinesin-like 1.

| SITEID | TARGET SEQ ID NO | TARGET SITE | SEQUENCE | REV COMP OF SEQ ID | ACTIVE IN | SEQ ID NO |
|---|---|---|---|---|---|---|
| 99233 | 3 | 1341 | aaaatgaacttgaccagtgt | 29 | H. sapiens | 61 |
| 99235 | 3 | 2119 | gcaatgtggaaacctaactg | 31 | H. sapiens | 62 |
| 99237 | 3 | 1053 | gtacattggaatatgctcat | 33 | H. sapiens | 63 |
| 99238 | 3 | 536 | tctgatgtttctgagagact | 34 | H. sapiens | 64 |
| 99239 | 3 | 394 | agaggatcccttggctggta | 35 | H. sapiens | 65 |
| 99241 | 3 | 1619 | aacctgaatagtctgtttaa | 37 | H. sapiens | 66 |
| 99242 | 3 | 2960 | ctggggcagtatactgaaga | 38 | H. sapiens | 67 |
| 99244 | 3 | 1159 | acgtttaaaacgagatcttg | 40 | H. sapiens | 68 |
| 99246 | 3 | 2260 | tgtccaggaaaatatacagc | 42 | H. sapiens | 69 |
| 99248 | 3 | 2333 | gctgattctgatggcttctc | 44 | H. sapiens | 70 |
| 99249 | 3 | 1023 | ctgcatctctcaatcttgag | 45 | H. sapiens | 71 |
| 99250 | 3 | 2620 | taaggcagctcatgagaaac | 46 | H. sapiens | 72 |

As these "preferred target regions" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these sites and consequently inhibit the expression of kinesin-like 1.

Example 16

Western Blot Analysis of Kinesin-Like 1 Protein Levels

Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to kinesin-like 1 is used, with a radiolabeled or fluorescently labeled secondary antibody directed against the primary antibody species. Bands are visualized using a PHOSPHORIM-AGER™ (Molecular Dynamics, Sunnyvale Calif.).

Example 17

Cell Cycle Assay and Flow Cytometry Analysis

The measurement of the DNA content of cells can provide a great deal of information about the cell cycle, and consequently the effect on the cell cycle of added stimuli (e.g. transfected genes or drug treatment). Therefore, in a further embodiment of the invention, antisense compounds were analyzed for their effects on the cell cycle (DNA content) by fluorescence-activated cell sorting (FACS) analysis in MCF-7, T47D and HMEC cells. This analysis is based on the principle that the DNA content of a cell changes through the progression of the cell cycle and that this change can be quantitated by staining the DNA and measuring the amount of stain over a period of time. Flow cytometry (FACS) is a means of measuring certain physical and chemical characteristics, such as the DNA content, of cells or particles as they travel in suspension one by one past a sensing point.

When cells reached 70% confluency, they were treated with antisense oligonucleotide (ISIS 183881, SEQ ID NO: 15) or a control oligonucleotide, ISIS 29848, a 20-mer random oligonucleotide (NNNNNNNNNNNNNNNNNNNN, wherein each N can be A, C, G or T; herein incorporated as SEQ ID NO: 73) as described in other examples herein. For cells grown in 96-well plates, wells were washed once with 100 µL OPTI-MEM™-1 reduced-serum medium (Invitrogen Corporation, Carlsbad, Calif.) and then treated with 130 µL of OPTI-MEM™-1 containing 3.75 µg/mL LIPOFECTIN™ (Invitrogen Corporation, Carlsbad, Calif.) and the desired concentration of oligonucleotide. After 4–7 hours of treatment, the medium was replaced with fresh medium. Cells were harvested 16–24 hours after oligonucleotide treatment and the growth medium (including floating cells) were transferred to fluorescence-activated cell sorting (FACS) tubes. The remaining cells were detached from the plates with gentle tapping and were washed with 250 ul PBS/5 mM EDTA. Following the wash, 250 ul trypsin was added to the cells and incubated at room temperature for 5 minutes. These cells were then added to the FACS tubes. Tubes were spun in a tabletop centrifuge at 2000 rpm for 5 minutes and the supernatant was decanted.

Cells were then washed with 2 ml PBS/5 mM EDTA and the tubes were spun again at 2000 rpm for 5 minutes with the supernatant being decanted after centrifugation. Cells were then resuspended with 0.4 ml PBS/5 mM EDTA and briefly vortexed. Following resuspension and vortexing, 1.6 mls cold ethanol was added while the tube was again gently vortexed. Cells were stored at −20° C. overnight. The following day, tubes were spun at 2000 rpm and the supernatant was decanted. Cells were then washed with 2 mls PBS/5 mM EDTA and resuspended with 0.15 ml PI mix (100 ug/ml propidium iodide, 1:200 RNAse cocktail; Ambion, Inc. (Austin, Tex.), Catalog Number # 2286). Samples were then run on a flow cytometer and the data were analyzed via the ModFit™ algorithm (AMPL Software Pty Ltd, Turramurra, Australia) to determine the distribution of cells in subG1, G1-, S- and G2M-phases of mitosis. The percent of cells arrested in the G2M phase of the cell cycle for each cell line is shown in Table 3. Data are compared to untreated controls (UTC) and the control antisense oligonucleotide, ISIS 29848. Data are an average of two assays.

TABLE 3

Percent Arrest in G2M phase of the cell cycle by ISIS 147764

| Cell line | UTC | Control; ISIS 29848 | ISIS 183881 |
|---|---|---|---|
| | | Percent G2M Arrest | |
| MCF-7 | 7 | 8 | 23 |
| T47D | 15 | 20 | 45 |
| HMEC | 14 | 15 | 28 |

These data indicate that ISIS 183881 was able to arrest cancer cells in the G2M phase of the cell cycle. It was also demonstrated that this antisense compound had no effect on cell polyploidy. These data are shown in Table 4.

TABLE 4

Percent Arrest in G2M phase of the cell cycle by ISIS 147764

| Cell line | UTC | Control; ISIS 29848 | ISIS 183881 |
|---|---|---|---|
| | | Percent Polyploidy | |
| MCF-7 | 12 | 13 | 14 |
| T47D | 19 | 23 | 20 |
| HMEC | 3 | 4 | 5 |

These data indicate that the antisense compound, ISIS 183881 did not induce the production of multiple nucleii, but in fact arrested cells prior to mitosis.

What is claimed is:

1. A compound 8 to 80 nucleobases in length targeted to a nucleic acid molecule encoding kinesin-like 1, wherein said compound specifically hybridizes-within a region of SEQ ID NO: 3 of said nucleic acid molecule encoding kinesin-like 1 and inhibits the expression of kinesin-like 1, and wherein said compound comprises at least an 8-nucleobase portion of SEQ ID NO: 25, 15 or 22.

2. The compound of claim 1 which is an antisense oligonucleotide.

3. The compound of claim 2 wherein the antisense oligonucleotide comprises at least one modified internucleoside linkage.

4. The compound of claim 3 wherein the modified internucleoside linkage is a phosphorothioate linkage.

5. The compound of claim 2 wherein the antisense oligonucleotide comprises at least one modified sugar moiety.

6. The compound of claim 5 wherein the modified sugar moiety is a 2'-O-methoxyethyl sugar moiety.

7. The compound of claim 2 wherein the antisense oligonucleotide comprises at least one modified nucleobase.

8. The compound of claim 7 wherein the modified nucleobase is a 5-methylcytosine.

9. The compound of claim 2 wherein the antisense oligonucleotide is a chimeric oligonucleotide.

10. A composition comprising the compound of claim 1 and a pharmaceutically acceptable carrier or diluent.

11. The composition of claim 10 further comprising a colloidal dispersion system.

12. The composition of claim 10 wherein the compound is an antisense oligonucleotide.

13. A method of inhibiting the expression of kinesin-like 1 in cells or tissues comprising contacting said cells or tissues with the compound of claim 1 so that expression of kinesin-like 1 is inhibited.

14. A method of treating an animal having a disease or condition associated with kinesin-like 1 comprising administering to said animal a therapeutically or prophylactically effective amount of the compound of claim 1 so that expression of kinesin-like 1 is inhibited.

15. The method of claim 14 wherein the disease or condition is a hyperproliferative disorder.

16. The method of claim 15 wherein the hyperproliferative disorder is cancer.

17. The method of claim 14 wherein the disease or condition is an autoimmune disease.

18. A method of arresting the cell cycle comprising administering the compound of claim 1.

19. The method of claim 18 wherein said cell cycle is arrested at the G2M phase.

* * * * *

SEQUENCE LISTING

```
<160> NUMBER OF SEQ ID NOS: 73

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                           20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                           20

<210> SEQ ID NO 3
<211> LENGTH: 3741
<212> TYPE: DNA
<213> ORGANISM: Homo sapiens
<220> FEATURE:
<221> NAME/KEY: CDS
<222> LOCATION: (11)...(3184)

<400> SEQUENCE: 3
gaattccgtc atg gcg tcg cag cca aat tcg tct gcg aag aag aaa gag    49
            Met Ala Ser Gln Pro Asn Ser Ser Ala Lys Lys Lys Glu
              1               5                  10 gag aag ggg aag aac atc cag gtg gtg gtg aga tgc aga cca ttt aat   97
```

-continued

| | | |
|---|---|---|
| Glu Lys Gly Lys Asn Ile Gln Val Val Val Arg Cys Arg Pro Phe Asn<br>15                      20                      25 | | |
| ttg gca gag cgg aaa gct agc gcc cat tca ata gta gaa tgt gat cct<br>Leu Ala Glu Arg Lys Ala Ser Ala His Ser Ile Val Glu Cys Asp Pro<br>30                      35                      40                      45 | 145 |
| gta cga aaa gaa gtt agt gta cga act gga gga ttg gct gac aag agc<br>Val Arg Lys Glu Val Ser Val Arg Thr Gly Gly Leu Ala Asp Lys Ser<br>50                      55                      60 | 193 |
| tca agg aaa aca tac act ttt gat atg gtg ttt gga gca tct act aaa<br>Ser Arg Lys Thr Tyr Thr Phe Asp Met Val Phe Gly Ala Ser Thr Lys<br>65                      70                      75 | 241 |
| cag att gat gtt tac cga agt gtt gtt tgt cca att ctg gat gaa gtt<br>Gln Ile Asp Val Tyr Arg Ser Val Val Cys Pro Ile Leu Asp Glu Val<br>80                      85                      90 | 289 |
| att atg ggc tat aat tgc act atc ttt gcg tat ggc caa act ggc act<br>Ile Met Gly Tyr Asn Cys Thr Ile Phe Ala Tyr Gly Gln Thr Gly Thr<br>95                      100                   105 | 337 |
| gga aaa act ttt aca atg gaa ggt gaa agg tca cct aat gaa gag tat<br>Gly Lys Thr Phe Thr Met Glu Gly Glu Arg Ser Pro Asn Glu Glu Tyr<br>110                    115                   120                125 | 385 |
| acc tgg gaa gag gat ccc ttg gct ggt ata att cca cgt acc ctt cat<br>Thr Trp Glu Glu Asp Pro Leu Ala Gly Ile Ile Pro Arg Thr Leu His<br>130                    135                   140 | 433 |
| caa att ttt gag aaa ctt act gat aat ggt act gaa ttt tca gtc aaa<br>Gln Ile Phe Glu Lys Leu Thr Asp Asn Gly Thr Glu Phe Ser Val Lys<br>145                      150                   155 | 481 |
| gtg tct ctg ttg gag atc tat aat gaa gag ctt ttt gat ctt ctt aat<br>Val Ser Leu Leu Glu Ile Tyr Asn Glu Glu Leu Phe Asp Leu Leu Asn<br>160                    165                   170 | 529 |
| cca tca tct gat gtt tct gag aga cta cag atg ttt gat gat ccc cgt<br>Pro Ser Ser Asp Val Ser Glu Arg Leu Gln Met Phe Asp Asp Pro Arg<br>175                      180                   185 | 577 |
| aac aag aga gga gtg ata att aaa ggt tta gaa gaa att aca gta cac<br>Asn Lys Arg Gly Val Ile Ile Lys Gly Leu Glu Glu Ile Thr Val His<br>190                    195                   200                205 | 625 |
| aac aag gat gaa gtc tat caa att tta gaa aag ggg gca gca aaa agg<br>Asn Lys Asp Glu Val Tyr Gln Ile Leu Glu Lys Gly Ala Ala Lys Arg<br>210                    215                   220 | 673 |
| aca act gca gct act ctg atg aat gca tac tct agt cgt tcc cac tca<br>Thr Thr Ala Ala Thr Leu Met Asn Ala Tyr Ser Ser Arg Ser His Ser<br>225                      230                   235 | 721 |
| gtt ttc tct gtt aca ata cat atg aaa gaa act acg att gat gga gaa<br>Val Phe Ser Val Thr Ile His Met Lys Glu Thr Thr Ile Asp Gly Glu<br>240                      245                   250 | 769 |
| gag ctt gtt aaa atc gga aag ttg aac ttg gtt gat ctt gca gga agt<br>Glu Leu Val Lys Ile Gly Lys Leu Asn Leu Val Asp Leu Ala Gly Ser<br>255                      260                   265 | 817 |
| gaa aac att ggc cgt tct gga gct gtt gat aag aga gct cgg gaa gct<br>Glu Asn Ile Gly Arg Ser Gly Ala Val Asp Lys Arg Ala Arg Glu Ala<br>270                    275                   280                285 | 865 |
| gga aat ata aat caa tcc ctg ttg act ttg gga agg gtc att act gcc<br>Gly Asn Ile Asn Gln Ser Leu Leu Thr Leu Gly Arg Val Ile Thr Ala<br>290                    295                   300 | 913 |
| ctt gta gaa aga aca cct cat gtt cct tat cga gaa tct aaa cta act<br>Leu Val Glu Arg Thr Pro His Val Pro Tyr Arg Glu Ser Lys Leu Thr<br>305                    310                   315 | 961 |
| aga atc ctc cag gat tct ctt gga ggg cgt aca aga aca tct ata att<br>Arg Ile Leu Gln Asp Ser Leu Gly Gly Arg Thr Arg Thr Ser Ile Ile<br>320                    325                   330 | 1009 |

```
                                    -continued gca aca att tct cct gca tct ctc aat ctt gag gaa act ctg agt aca      1057
Ala Thr Ile Ser Pro Ala Ser Leu Asn Leu Glu Glu Thr Leu Ser Thr
335                 340                 345 ttg gaa tat gct cat aga gca aag aac ata ttg aat aag cct gaa gtg      1105
Leu Glu Tyr Ala His Arg Ala Lys Asn Ile Leu Asn Lys Pro Glu Val
350                 355                 360                 365 aat cag aaa ctc acc aaa aaa gct ctt att aag gag tat acg gag gag      1153
Asn Gln Lys Leu Thr Lys Lys Ala Leu Ile Lys Glu Tyr Thr Glu Glu
                370                 375                 380 ata gaa cgt tta aaa cga gat ctt gct gca gcc cgt gag aaa aat gga      1201
Ile Glu Arg Leu Lys Arg Asp Leu Ala Ala Ala Arg Glu Lys Asn Gly
            385                 390                 395 gtg tat att tct gaa gaa aat ttt aga gtc atg agt gga aaa tta act      1249
Val Tyr Ile Ser Glu Glu Asn Phe Arg Val Met Ser Gly Lys Leu Thr
        400                 405                 410 gtt caa gaa gag cag att gta gaa ttg att gaa aaa att ggt gct gtt      1297
Val Gln Glu Glu Gln Ile Val Glu Leu Ile Glu Lys Ile Gly Ala Val
415                 420                 425 gag gag gag ctg aat agg gtt aca gag ttg ttt atg gat aat aaa aat      1345
Glu Glu Glu Leu Asn Arg Val Thr Glu Leu Phe Met Asp Asn Lys Asn
430                 435                 440                 445 gaa ctt gac cag tgt aaa tct gac ctg caa aat aaa aca caa gaa ctt      1393
Glu Leu Asp Gln Cys Lys Ser Asp Leu Gln Asn Lys Thr Gln Glu Leu
                450                 455                 460 gaa acc act caa aaa cat ttg caa gaa act aaa tta caa ctt gtt aaa      1441
Glu Thr Thr Gln Lys His Leu Gln Glu Thr Lys Leu Gln Leu Val Lys
            465                 470                 475 gaa gaa tat atc aca tca gct ttg gaa agt act gag gag aaa ctt cat      1489
Glu Glu Tyr Ile Thr Ser Ala Leu Glu Ser Thr Glu Glu Lys Leu His
        480                 485                 490 gat gct gcc agc aag ctg ctt aac aca gtt gaa gaa act aca aaa gat      1537
Asp Ala Ala Ser Lys Leu Leu Asn Thr Val Glu Glu Thr Thr Lys Asp
495                 500                 505 gta tct ggt ctc cat tcc aaa ctg gat cgt aag aag gca gtt gac caa      1585
Val Ser Gly Leu His Ser Lys Leu Asp Arg Lys Lys Ala Val Asp Gln
510                 515                 520                 525 cac aat gca gaa gct cag gat att ttt ggc aaa aac ctg aat agt ctg      1633
His Asn Ala Glu Ala Gln Asp Ile Phe Gly Lys Asn Leu Asn Ser Leu
                530                 535                 540 ttt aat aat atg gaa gaa tta att aag gat ggc agc tca aag caa aag      1681
Phe Asn Asn Met Glu Glu Leu Ile Lys Asp Gly Ser Ser Lys Gln Lys
            545                 550                 555 gcc atg cta gaa gta cat aag acc tta ttt ggt aat ctg ctg tct tcc      1729
Ala Met Leu Glu Val His Lys Thr Leu Phe Gly Asn Leu Leu Ser Ser
        560                 565                 570 agt gtc tct gca tta gat acc att act aca gta gca ctt gga tct ctc      1777
Ser Val Ser Ala Leu Asp Thr Ile Thr Thr Val Ala Leu Gly Ser Leu
575                 580                 585 aca tct att cca gaa aat gtg tct act cat gtt tct cag att ttt aat      1825
Thr Ser Ile Pro Glu Asn Val Ser Thr His Val Ser Gln Ile Phe Asn
590                 595                 600                 605 atg ata cta aaa gaa caa tca tta gca gca gaa agt aaa act gta cta      1873
Met Ile Leu Lys Glu Gln Ser Leu Ala Ala Glu Ser Lys Thr Val Leu
                610                 615                 620 cag gaa ttg att aat gta ctc aag act gat ctt cta agt tca ctg gaa      1921
Gln Glu Leu Ile Asn Val Leu Lys Thr Asp Leu Leu Ser Ser Leu Glu
            625                 630                 635 atg att tta tcc cca act gtg gtg tct ata ctg aaa atc aat agt caa      1969
Met Ile Leu Ser Pro Thr Val Val Ser Ile Leu Lys Ile Asn Ser Gln
        640                 645                 650
```

```
cta aag cat att ttc aag act tca ttg aca gtg gcc gat aag ata gaa    2017
Leu Lys His Ile Phe Lys Thr Ser Leu Thr Val Ala Asp Lys Ile Glu
    655                 660                 665 gat caa aaa aaa agg aac tca gat ggc ttt ctc agt ata ctg tgt aac    2065
Asp Gln Lys Lys Arg Asn Ser Asp Gly Phe Leu Ser Ile Leu Cys Asn
670                 675                 680                 685 aat cta cat gaa cta caa gaa aat acc att tgt tcc ttg gtt gag tca    2113
Asn Leu His Glu Leu Gln Glu Asn Thr Ile Cys Ser Leu Val Glu Ser
                690                 695                 700 caa aag caa tgt gga aac cta act gaa gac ctg aag aca ata aag cag    2161
Gln Lys Gln Cys Gly Asn Leu Thr Glu Asp Leu Lys Thr Ile Lys Gln
            705                 710                 715 acc cat tcc cag gaa ctt tgc aag tta atg aat ctt tgg aca gag aga    2209
Thr His Ser Gln Glu Leu Cys Lys Leu Met Asn Leu Trp Thr Glu Arg
        720                 725                 730 ttc tgt gct ttg gag gaa aag tgt gaa aat ata cag aaa cca ctt agt    2257
Phe Cys Ala Leu Glu Glu Lys Cys Glu Asn Ile Gln Lys Pro Leu Ser
    735                 740                 745 agt gtc cag gaa aat ata cag cag aaa tct aag gat ata gtc aac aaa    2305
Ser Val Gln Glu Asn Ile Gln Gln Lys Ser Lys Asp Ile Val Asn Lys
750                 755                 760                 765 atg act ttt cac agt caa aaa ttt tgt gct gat tct gat ggc ttc tca    2353
Met Thr Phe His Ser Gln Lys Phe Cys Ala Asp Ser Asp Gly Phe Ser
                770                 775                 780 cag gaa ctc aga aat ttt aac caa gaa ggt aca aaa ttg gtt gaa gaa    2401
Gln Glu Leu Arg Asn Phe Asn Gln Glu Gly Thr Lys Leu Val Glu Glu
            785                 790                 795 tct gtg aaa cac tct gat aaa ctc aat ggc aac ctg gaa aaa ata tct    2449
Ser Val Lys His Ser Asp Lys Leu Asn Gly Asn Leu Glu Lys Ile Ser
        800                 805                 810 caa gag act gaa cag aga tgt gaa tct ctg aac aca aga aca gtt tat    2497
Gln Glu Thr Glu Gln Arg Cys Glu Ser Leu Asn Thr Arg Thr Val Tyr
    815                 820                 825 ttt tct gaa cag tgg gta tct tcc tta aat gaa agg gaa cag gaa ctt    2545
Phe Ser Glu Gln Trp Val Ser Ser Leu Asn Glu Arg Glu Gln Glu Leu
830                 835                 840                 845 cac aac tta ttg gag gtt gta agc caa tgt tgt gag gct tca agt tca    2593
His Asn Leu Leu Glu Val Val Ser Gln Cys Cys Glu Ala Ser Ser Ser
                850                 855                 860 gac atc act gag aaa tca gat gga cgt aag gca gct cat gag aaa cag    2641
Asp Ile Thr Glu Lys Ser Asp Gly Arg Lys Ala Ala His Glu Lys Gln
            865                 870                 875 cat aac att ttt ctt gat cag atg act att gat gaa gat aaa ttg ata    2689
His Asn Ile Phe Leu Asp Gln Met Thr Ile Asp Glu Asp Lys Leu Ile
        880                 885                 890 gca caa aat cta gaa ctt aat gaa acc ata aaa att ggt ttg act aag    2737
Ala Gln Asn Leu Glu Leu Asn Glu Thr Ile Lys Ile Gly Leu Thr Lys
    895                 900                 905 ctt aat tgc ttt ctg gaa cag gat ctg aaa ctg gat atc cca aca ggt    2785
Leu Asn Cys Phe Leu Glu Gln Asp Leu Lys Leu Asp Ile Pro Thr Gly
910                 915                 920                 925 acg aca cca cag agg aaa agt tat tta tac cca tca acg ctg gta aga    2833
Thr Thr Pro Gln Arg Lys Ser Tyr Leu Tyr Pro Ser Thr Leu Val Arg
                930                 935                 940 act gaa cca cgt gaa cat ctc ctt gat cag ctg aaa agg aaa cag cct    2881
Thr Glu Pro Arg Glu His Leu Leu Asp Gln Leu Lys Arg Lys Gln Pro
            945                 950                 955 gag ctg tta atg atg cta aac tgt tca gaa aac aac aaa gaa gag aca    2929
Glu Leu Leu Met Met Leu Asn Cys Ser Glu Asn Asn Lys Glu Glu Thr
```

```
                    960               965              970
att ccg gat gtg gat gta gaa gag gca gtt ctg ggg cag tat act gaa      2977
Ile Pro Asp Val Asp Val Glu Glu Ala Val Leu Gly Gln Tyr Thr Glu
    975              980              985 gaa cct cta agt caa gag cca tct gta gat gct ggt gtg gat tgt tca      3025
Glu Pro Leu Ser Gln Glu Pro Ser Val Asp Ala Gly Val Asp Cys Ser
990              995              1000             1005 tca att ggc ggg gtt cca ttt ttc cag cat aaa aaa tca cat gga aaa      3073
Ser Ile Gly Gly Val Pro Phe Phe Gln His Lys Lys Ser His Gly Lys
            1010             1015             1020 gac aaa gaa aac aga ggc att aac aca ctg gag agg tct aaa gtg aa       3121
Asp Lys Glu Asn Arg Gly Ile Asn Thr Leu Glu Arg Ser Lys Val Glu
        1025             1030             1035 gaa act aca gag cac ttg gtt aca aag agc aga tta cct ctg cga gcc      3169
Glu Thr Thr Glu His Leu Val Thr Lys Ser Arg Leu Pro Leu Arg Ala
    1040             1045             1050 cag atc aac ctt taa ttcacttggg ggttggcaat tttatttta aagaaaaact       3224
Gln Ile Asn Leu  *
    1055 taaaaataaa acctgaaacc ccagaacttg agccttgtgt atagatttta aagaatata     3284
tatatcagcc gggcgcgtgg ctctagctgt aatcccagct aactttggag gctgaggcgg    3344
gtggattgct tgagcccagg agtttgagac cagcctggcc aacgtgcgct aaaaccttcg    3404
tctctgttaa aaattagccg ggcgtggtgg gcacactcct gtaatcccag ctactgggga    3464
ggctgaggca cgagaatcac ttgaacccag aagcgggggtt gcagtgagcc aaaggtacac   3524
cactacactc cagcctgggc aacagagcaa gactcggtct caaaaataaa atttaaaaaa    3584
gatataaggc agtactgtaa attcagttga attttgatat ctacccattt ttctgtcatc    3644
cctatagttc actttgtatt aaattggggtt tcatttggga tttgcaatgt aaatacgtat   3704
ttctagtttt catataaagt agttcttttta ggaattc                            3741

<210> SEQ ID NO 4
<211> LENGTH: 24
<212> TYPE: DNA
<213> ORGANISM: Artificial Sequence
<220> FEATURE:
<223> OTHER INFORMATION: PCR Primer

<400> SEQUENCE: 4
gtggtgagat gcagaccatt taat                                              24

<210> SEQ ID NO 5
<211> LENGTH: 30
<212> TYPE: DNA
<213> ORGANISM: Artificial Sequence
<220> FEATURE:
<223> OTHER INFORMATION: PCR Primer

<400> SEQUENCE: 5
cttttcgtac aggatcacat tctactattg                                        30

<210> SEQ ID NO 6
<211> LENGTH: 22
<212> TYPE: DNA
<213> ORGANISM: Artificial Sequence
<220> FEATURE:
<223> OTHER INFORMATION: PCR Probe

<400> SEQUENCE: 6
tggcagagcg gaaagctagc gc                                                22
```

```
<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                                                    19

<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc                                                   20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                                   20

<210> SEQ ID NO 10
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 10
tgttgactat atccttagat                                                   20

<210> SEQ ID NO 11
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 11
tctgctgcta atgattgttc                                                   20

<210> SEQ ID NO 12
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 12
ctggaataga tgtgagagat                                                   20

<210> SEQ ID NO 13
<211> LENGTH: 20
<212> TYPE: DNA
<213> ORGANISM: Artificial Sequence
<220> FEATURE:
```

<223> OTHER INFORMATION: Antisense Oligonucleotide

<400> SEQUENCE: 13
aaagtcaaca gggattgatt                                           20

<210> SEQ ID NO 14
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 14
gatcaagaaa aatgttatgc                                           20

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15
atccaagtgc tactgtagta                                           20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
tttcctcaag attgagagat                                           20

<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
caaagcacag aatctctctg                                           20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
cattaacttg caaagttcct                                           20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
atccagtttg gaatggagac                                           20

```
<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
ttagcatcat taacagctca                                            20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
taaacaactc tgtaacccta                                            20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
agaaacatca gatgatggat                                            20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 23
agtgaactta gaagatcagt                                            20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
ttcagctgat caaggagatg                                            20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
ccgagctctc ttatcaacag                                            20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 26
agcttctgca ttgtgttggt                                              20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
attcaactga atttacagta                                              20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
cagaggtaat ctgctctttg                                              20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
acactggtca agttcatttt                                              20

<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
cagtactttc caaagctgat                                              20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
cagttaggtt tccacattgc                                              20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
ctactttata tgaaaactag                                              20

<210> SEQ ID NO 33
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 33
atgagcatat tccaatgtac                                               20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
agtctctcag aaacatcaga                                               20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
taccagccaa gggatcctct                                               20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 36
ttcattatag atctccaaca                                               20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
ttaaacagac tattcaggtt                                               20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
tcttcagtat actgccccag                                               20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
```

```
actgtgaaaa gtcattttgt                                               20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
caagatctcg ttttaaacgt                                               20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
tggccatacg caaagatagt                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
gctgtatatt ttcctggaca                                               20

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
ttgctttgag ctgccatcct                                               20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
gagaagccat cagaatcagc                                               20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
ctcaagattg agagatgcag                                               20

<210> SEQ ID NO 46
<211> LENGTH: 20
<212> TYPE: DNA
<213> ORGANISM: Artificial Sequence
```

```
<220> FEATURE:
<223> OTHER INFORMATION: Antisense Oligonucleotide

<400> SEQUENCE: 46
gtttctcatg agctgcctta                                                20

<210> SEQ ID NO 47
<211> LENGTH: 20
<212> TYPE: DNA
<213> ORGANISM: H. sapiens
<220> FEATURE:

<400> SEQUENCE: 47
gaacaatcat tagcagcaga                                                20

<210> SEQ ID NO 48
<211> LENGTH: 20
<212> TYPE: DNA
<213> ORGANISM: H. sapiens
<220> FEATURE:

<400> SEQUENCE: 48
atctctcaca tctattccag                                                20

<210> SEQ ID NO 49
<211> LENGTH: 20
<212> TYPE: DNA
<213> ORGANISM: H. sapiens
<220> FEATURE:

<400> SEQUENCE: 49
aatcaatccc tgttgacttt                                                20

<210> SEQ ID NO 50
<211> LENGTH: 20
<212> TYPE: DNA
<213> ORGANISM: H. sapiens
<220> FEATURE:

<400> SEQUENCE: 50
gcataacatt tttcttgatc                                                20

<210> SEQ ID NO 51
<211> LENGTH: 20
<212> TYPE: DNA
<213> ORGANISM: H. sapiens
<220> FEATURE:

<400> SEQUENCE: 51
tactacagta gcacttggat                                                20

<210> SEQ ID NO 52
<211> LENGTH: 20
<212> TYPE: DNA
<213> ORGANISM: H. sapiens
<220> FEATURE:

<400> SEQUENCE: 52
atctctcaat cttgaggaaa                                                20

<210> SEQ ID NO 53
<211> LENGTH: 20
<212> TYPE: DNA
<213> ORGANISM: H. sapiens
<220> FEATURE:
```

<400> SEQUENCE: 53
cagagagatt ctgtgctttg                    20

<210> SEQ ID NO 54
<211> LENGTH: 20
<212> TYPE: DNA
<213> ORGANISM: H. sapiens
<220> FEATURE:

<400> SEQUENCE: 54
tgagctgtta atgatgctaa                    20

<210> SEQ ID NO 55
<211> LENGTH: 20
<212> TYPE: DNA
<213> ORGANISM: H. sapiens
<220> FEATURE:

<400> SEQUENCE: 55
atccatcatc tgatgtttct                    20

<210> SEQ ID NO 56
<211> LENGTH: 20
<212> TYPE: DNA
<213> ORGANISM: H. sapiens
<220> FEATURE:

<400> SEQUENCE: 56
actgatcttc taagttcact                    20

<210> SEQ ID NO 57
<211> LENGTH: 20
<212> TYPE: DNA
<213> ORGANISM: H. sapiens
<220> FEATURE:

<400> SEQUENCE: 57
catctccttg atcagctgaa                    20

<210> SEQ ID NO 58
<211> LENGTH: 20
<212> TYPE: DNA
<213> ORGANISM: H. sapiens
<220> FEATURE:

<400> SEQUENCE: 58
ctgttgataa gagagctcgg                    20

<210> SEQ ID NO 59
<211> LENGTH: 20
<212> TYPE: DNA
<213> ORGANISM: H. sapiens
<220> FEATURE:

<400> SEQUENCE: 59
accaacacaa tgcagaagct                    20

<210> SEQ ID NO 60
<211> LENGTH: 20
<212> TYPE: DNA
<213> ORGANISM: H. sapiens
<220> FEATURE:

<400> SEQUENCE: 60
caaagagcag attacctctg                                            20

<210> SEQ ID NO 61
<211> LENGTH: 20
<212> TYPE: DNA
<213> ORGANISM: H. sapiens
<220> FEATURE:

<400> SEQUENCE: 61
aaaatgaact tgaccagtgt                                            20

<210> SEQ ID NO 62
<211> LENGTH: 20
<212> TYPE: DNA
<213> ORGANISM: H. sapiens
<220> FEATURE:

<400> SEQUENCE: 62
gcaatgtgga aacctaactg                                            20

<210> SEQ ID NO 63
<211> LENGTH: 20
<212> TYPE: DNA
<213> ORGANISM: H. sapiens
<220> FEATURE:

<400> SEQUENCE: 63
gtacattgga atatgctcat                                            20

<210> SEQ ID NO 64
<211> LENGTH: 20
<212> TYPE: DNA
<213> ORGANISM: H. sapiens
<220> FEATURE:

<400> SEQUENCE: 64
tctgatgttt ctgagagact                                            20

<210> SEQ ID NO 65
<211> LENGTH: 20
<212> TYPE: DNA
<213> ORGANISM: H. sapiens
<220> FEATURE:

<400> SEQUENCE: 65
agaggatccc ttggctggta                                            20

<210> SEQ ID NO 66
<211> LENGTH: 20
<212> TYPE: DNA
<213> ORGANISM: H. sapiens
<220> FEATURE:

<400> SEQUENCE: 66
aacctgaata gtctgtttaa                                            20

<210> SEQ ID NO 67
<211> LENGTH: 20
<212> TYPE: DNA
<213> ORGANISM: H. sapiens
<220> FEATURE:

<400> SEQUENCE: 67
ctggggcagt atactgaaga                                            20

<210> SEQ ID NO 68
<211> LENGTH: 20
<212> TYPE: DNA
<213> ORGANISM: H. sapiens
<220> FEATURE:

<400> SEQUENCE: 68
acgtttaaaa cgagatcttg                                              20

<210> SEQ ID NO 69
<211> LENGTH: 20
<212> TYPE: DNA
<213> ORGANISM: H. sapiens
<220> FEATURE:

<400> SEQUENCE: 69
tgtccaggaa aatatacagc                                              20

<210> SEQ ID NO 70
<211> LENGTH: 20
<212> TYPE: DNA
<213> ORGANISM: H. sapiens
<220> FEATURE:

<400> SEQUENCE: 70
gctgattctg atggcttctc                                              20

<210> SEQ ID NO 71
<211> LENGTH: 20
<212> TYPE: DNA
<213> ORGANISM: H. sapiens
<220> FEATURE:

<400> SEQUENCE: 71
ctgcatctct caatcttgag                                              20

<210> SEQ ID NO 72
<211> LENGTH: 20
<212> TYPE: DNA
<213> ORGANISM: H. sapiens
<220> FEATURE:

<400> SEQUENCE: 72
taaggcagct catgagaaac                                              20

<210> SEQ ID NO 73
<211> LENGTH: 20
<212> TYPE: DNA
<213> ORGANISM: Artificial Sequence
<220> FEATURE:
<221> NAME/KEY: unsure
<222> LOCATION: (1)..(20)
<223> OTHER INFORMATION: Antisense Oligonucleotide

<400> SEQUENCE: 73
nnnnnnnnnn nnnnnnnnnn                                              20